(12) United States Patent
Maroun

(10) Patent No.: US 7,887,814 B2
(45) Date of Patent: *Feb. 15, 2011

(54) INTERFERON ANTAGONISTS USEFUL FOR THE TREATMENT OF INTERFERON RELATED DISEASES

(75) Inventor: Leonard E. Maroun, Lawrence, MA (US)

(73) Assignee: Meiogen Biotechnology Corporation, Beverly, MA (US)

( * ) Notice: Subject to any disclaimer, the term of this patent is extended or adjusted under 35 U.S.C. 154(b) by 622 days.

This patent is subject to a terminal disclaimer.

(21) Appl. No.: 11/609,960

(22) Filed: Dec. 13, 2006

(65) Prior Publication Data
US 2007/0160609 A1    Jul. 12, 2007

Related U.S. Application Data

(60) Division of application No. 10/284,740, filed on Oct. 31, 2002, now Pat. No. 7,285,526, which is a continuation-in-part of application No. 09/845,260, filed on Apr. 30, 2001, now abandoned, which is a continuation of application No. 09/067,398, filed on Apr. 28, 1998, now abandoned, which is a continuation of application No. 08/502,519, filed on Jul. 14, 1995, now Pat. No. 5,780,027.

(51) Int. Cl.
*A61K 39/285* (2006.01)
*A61K 38/16* (2006.01)
(52) U.S. Cl. .................. 424/232.1; 424/278.1; 514/1.1
(58) Field of Classification Search ........................ None
See application file for complete search history.

(56) References Cited

U.S. PATENT DOCUMENTS

| | | | |
|---|---|---|---|
| 4,766,106 A | 8/1988 | Katre et al. | |
| 4,824,432 A | 4/1989 | Skurkovich et al. | |
| 4,948,738 A | 8/1990 | Banchereau et al. | |
| 4,973,556 A | 11/1990 | Bove et al. | |
| 5,297,562 A | 3/1994 | Potter | |
| 5,780,027 A | 7/1998 | Maroun | |
| 5,888,511 A | 3/1999 | Skurkovich et al. | |
| 6,093,405 A | 7/2000 | Zagury et al. | |
| 2006/0099224 A1 | 5/2006 | Kirn | |

FOREIGN PATENT DOCUMENTS

| | | | |
|---|---|---|---|
| EP | 0601052 | | 10/1996 |
| WO | WO 92/07944 | | 5/1992 |
| WO | WO 93/04699 | * | 3/1993 |
| WO | WO 00/40203 | * | 7/2000 |
| WO | WO 2004-014314 A2 | | 2/2004 |
| WO | WO 2004-014314 A3 | | 2/2004 |

OTHER PUBLICATIONS

Carel JC et al. Transforming growth factor beta decreases the immunogenicity of rat islet xenografts (rat to mouse) and prevents rejection in association with treatment of the recipient with a monoclonal antibody to interferon gamma. Proc Natl Acad Sci USA, 1990; 87:1591-1595.*

Malek-Hosseini S et al. Long-term results of renal transplantation: A single-center analysis of 1200 transplants. Transplantation Proc. 2006; 38;454-456.*

Wiseman LR and Faulds D. Daclizmab: A review of its use in the prevention of acute rejection in renal transplant recipients. Drugs, 1999; 58(6):1029-1042.*

Yamada, et al., Neurosci Lett. 1994; 7: 181: 61-64.

Li, et al., BMC Medical Genetics 2006; 7:24.

Skurkovich, et al., Ann. NY Acad. Sci 2005; 1051; 684-700.

O'Shea, J.J., et al., (2002), "Cytokines and Autoimmunity", *Nature Reviews Immunology*, 2:37-45.

Le Page C. et al., (2000), "Interferon activation and innate immunity", *Reviews in Immunogenetics*, 2:374-386.

Blasko, I. et al., (1999), "TNFα plus IFNγ induce the production of Alzheimer β-amyloid peptides and decrease the secretion of APPs", *The FASEB Journal*, 13:63-68.

Gringeri, A. et al., (1999), "Active Anti-Interferon-α Immunization: A European-Israeli, Randomized, Double-Blind, Placebo-Controlled Clinical Trial in 242 HIV-1-Infected Patients (the EURIS Study)", *Journal of Acquired Immune Deficiency Syndrome and Human Retrovirology*, 20(4):358-370.

Akwa, Y. et al., (1998), "Transgenic Expression of IFN-α in the Central Nervous System of Mice Protects Against Lethal Neurotropic Viral Infection but Induces Inflammation and Neurodegeneration", *The Journal of Acquired Immunology*, 161:5016-5026.

Maroun, L.E. et al., (1998), "The Untoward Side Effects of Interferon Therapy Correlate Well with the Spectrum of Symptoms that Make Up the Down Syndrome", *Down Syndrome Research and Practice*, 5(3):143-147.

Wiseman, B.F. et al., (1997), "Interferon and trisomy 16 mouse fetal heart development and function", *Cytogenet Cell Genet*, 77 (Suppl. 1):30(Abstract).

(Continued)

*Primary Examiner*—Elizabeth C. Kemmerer
*Assistant Examiner*—Kimberly A. Ballard
(74) *Attorney, Agent, or Firm*—Yankwich & Associates, P.C.; Leon R. Yankwich; Michael R. Wesolowski

(57) ABSTRACT

The present invention relates to a process for ameliorating or preventing diseases that are caused, in part, by an increased level of, and/or an abnormal responsivity to, interferon. Specifically, the invention provides compositions and methods for preventing and treating subjects suffering from, or at risk for, such diseases. Such methods include the administration of a pharmacological preparation of interferon binding proteins that antagonize interferon's action. This invention comprises compositions of interferon binding proteins that can inhibit the activity of Type I and II.

17 Claims, 14 Drawing Sheets

OTHER PUBLICATIONS

Gringeri, A. et al., (1996), "Absence of Clinical, Virological, and Immunological Signs of Progression in HIV-1-Infected Patients Receiving Active Anti-Interferon-α Immunization: A 30-Month Follow-Up Report", *Journal of Acquired Immune Deficiency Syndromes and Human Retrovirology*, 13(1):55-67.

Alcami, A. et al., (1995), "Vaccinia, Cowpox, and Camelpox Viruses Encode Soluble Gamma Interferon Receptors with Novel Broad Species Specificity", *Journal of Virology*, 69(8):4633-4639.

Fall, L.S. et al., (1995), "Biological effect of active anti-IFNα immunization in HIV-infected patients", *Biomed & Pharmacother*, 49:422-428.

Gringeri, A. et al., (1995), "Anti-Alpha Interferon Immunization: Safety and Immunogenicity in Asymptomatic HIV Positive Patients at High Risk of Disease Progression", *Cellular and Molecular Biology*, 41(3):381-387.

Moosmayer, D. et al., (1995), "A Bivalent Immunoadhesin of the Human Interferon-γ Activity", *Journal of Interferon and Cytokine Research*, 15:1111-1115.

Przemioslo, R.T. et al., (1995), "Historical changes in small bowel mucosa induced by gliadin sensitive T lymphocytes can be blocked by anti-interferon γ antibody", *Gut*, 36:874-879.

Symons, J.A. et al., (1995), "Vaccinia Virus Encodes a Soluble Type I Interferon Receptor of Novel Structure and Broad Species Specificity", *Cell*, 81:551-560.

Lachgar, A. et al., (1994), "Involvement of α-interferon in HIV-1 induced immunosuppression. A potential target for AIDS prophylaxis and treatment", *Biomed & Pharmacother*, 48:73-77.

Gringeri, A. et al., (1994), "A Randomized, Placebo-Controlled, Blind Anti-AIDS Clinical Trial: Safety and Immunogenicity of a Specific Anti-IFNα Immunization", *Journal of Acquired Immune Deficiency Syndromes*, 7(9):978-988.

Soh, J. et al., (1994), "Expression of a Functional Human Type I Interferon Receptor in Hamster Cells: Applicaton of Functional Yeast Artificial Chromosome (YAC) Screening", *The Journal of Biological Chemistry*, 269(27):18102-18110.

Youngman, K.R. et al., (1994), "Inhibition of IFN-γ Activity in Supernatants from Stimulated Human Intestinal Mononuclear Cells Prevents Up-Regulation of the Polymeric Ig Receptor in an Intestinal Epithelial Cell Line", *J. Immunology*, 153:675-681.

Gerdes, A.M. et al., (1993), "Effect of increased gene dosage expression on the α-interferon receptors in Down's Syndrome", *Biochimica et Biophysica Acta*, 1181:135-140.

Haak-Frendscho, M. et al., (1993), "Inhibition of interferon-γ by an interferon-γ receptor immunoadhesin", *Immunology*, 79:594-599.

Soh, J. et al., (1993), "Identification of a yeast artificial chromosome clone encoding an accessory factor for the human interferon γ receptor: Evidence for multiple accessory factors", *Proc. Natl. Acad. Sci. USA*, 90:8737-8741.

Holtzman, D.M. et al., (1992), "Dysregulation of gene expression in mouse trisomy 16, an animal model of Down Syndrome", *The EMBO Journal*, 11(2):619-627.

Sen, G.C. et al., (1992), "The Interferon System", *The Journal of Biological Chemistry*, 267(8):5017-5020.

Groner, Y. et al., (1990), "Down syndrome clinical symptoms are manifested in transfected cells and transgenic mice overexpressing the human Cu/Zn-superoxide dismutase gene", *J. Physiol. Paris*, 84:53-77.

Jung, V. et al., (1990), "Expression and Reconstitution of a Biologically Active Human Interferon-γ Receptor in Hamster cells",*The Journal of Biological Chemistry*, 265(4):1827-1830.

Kato, K. et al., (1990), "Enhancement of S-100β Protein in Blood of Patients with Down's Syndrome", *J. Mol. Neurosci.*, 2:109-113.

Mann, D.M.A. et al., (1990), "The prevalence of amyloid (A4) protein deposits within the cerebral and cerebellar cortex in Down's Syndrome and Alzheimer's disease",*Acta Neuropathol*, 80:318-327.

Bersu, E.T. et al., (1989), "Altered Placental Morphology Associated with Murine Trisomy 16 and Murine Trisomy 19", *Teratology*, 40:513-523.

Cronk, C. et al., (1988), "Growth Charts for Children with Down Syndrome: 1 Month to 18 Years of Age", *Pediatrics*, 81(1):102-110.

Plioplys, A.V., (1988), "Expression of the 210 kDa neurofilament subunit in cultured central nervous system from normal and trisomy 16 mice: regulation by interferon", *Journal of the Neurological Sciences*, 85:209-222.

Gearhart, J.D. et al., (1986), "Autosomal Aneuploidy in Mice: Generation and Developmental Consequences", *Brain Research Bulletin*, 16:789-801.

Wisniewski, K.E. et al., (1986), "Neuronal Density and Synaptogenesis in the Postnatal Stage of Brain Maturation in Down Syndrome", *The Neurobiology of Down Syndrome*, 29-44.

Carr, J., (1985), "The Development of Intelligence", *Current Approaches to Down Syndrome*, Chapter 10:167-186.

Dussaix, E. et al., (1985), "Intrathecal synthesis of different alpha-interferons in patients with various neurological diseases", *Acta Neurol. Scand.*, 71:504-509.

Raziuddin, A. et al., (1984), "Receptors for human α and β interferon but not for γ interferon are specified by human chromosome 21", *Proc. Natl. Acad. Sci. USA*, 81:5504-5508.

Backman, K. et al., (1981), "Physical and genetic characterization of the *glnA-glnG* region of the *Escherichia coli* chromonsome", *Proc. Natl. Acad. Sci. USA*, 78(6):3743-3747.

Maroun, L.E., (1980), "Interferon Action and Chromosome 21 Trisomy", *J. Theor. Biol.*, 86:603-606.

Gropp, A. et al., (1974), "Trisomy in the fetal backcross progeny of male and female metametacentric heterozygotes of the mouse.I", *Cytogenet. Cell Genet.*, 13:511-535.

Tan, Y.H. et al., (1974), "Human Chromosome 21 Dosage: Effect on the Expression of the Interferon Induced Antiviral State", *Science*, 186:61-63.

Tan, Y.H. et al., (1973), "The Linkage of Genes for the Human Interferon-Induced Antiviral Protein and Indophenol Oxidase-B Traits to Chromosome G-21", *The Journal of Experimental Medicine*, 137:317-330.

Biwas et al., J. of Exp. Med., Sep. 1, 1992, 176(3):739-50.

Capobianchi et al., AIDS Res. & Human Retroviruses, 9(10):957-62, 1993.

Colamonici et al., J. of Biol. Chem., Jul. 7, 1995, 270(27):15974-78.

Shin et al., PNAS 92:2820-2824, Mar. 1995.

U.S. Appl. No. 09/845,260, filed Jan. 30, 2003, Maroun, Leonard.

Maroun, Leonard E., "Anti-interferon Immunoglobulins Can Improve the Trisomy 16 Mouse Phenotype", Teratology, 1995, vol. 51, pp. 329-335.

Smith, Geoffrey L., "Interfering with Interferon by Vaccinia Virus", Immunology, 1996, vol. 89, p. 18.

Smith, Geoffrey L., "Vaccinia Virus Immune Evasion", Immunological Reviews, Oct. 1997, pp. 137-154.

Goodbourn, S. et al., "Interferons: Cell Signalling, Immune Modulation, Antiviral Responses and Virus Countermeasures", Oct. 2000, vol. 81, No. 10, pp. 2341-2364.

Alcami, Antonio, et al., "The Vaccinia Virus Soluble Alpha/Beta Interferon (IFN) Receptor Binds to the Cell Surface and Protects Cells from the Antiviral Effects of IFN", Dec. 2000, vol. 74, No. 23, pp. 11230-11239.

Symons, J A, et al., "Vaccinia Virus Encodes a Soluble Type I Interferon Receptor of Novel Structure and Broad Species Specificity", 1995, vol. 81, pp. 551-560.

Symons, J A, et al., "A Study of the Vaccinia Virus Interferon-Gamma Receptor and its Contribution to Virus Virulence", 2002, vol. 83, No. 8, pp. 1953-1964.

Supplementary Partial European Search Report for EP 03 77 9407, Aug. 6, 2007, p. 1-5.

* cited by examiner

GenBank Acc. No. M11026

```
MALSFSLLMA VLVLSYKSIC SLGCDLPQTH SLGNRRALIL LAQMGRISPF SCLKDRHDFG  60
LPQEEFDGNQ FQKTQAISVL HEMIQQTFNL FSTEDSSAAW EQSLLEKFST ELYQQLNNLE 120
ACVIQEVGME ETPLMNEDSI LAVRKYFQRI TLYLTEKKYS PCAWEVVRAE IMRSLSFSTN 180
LQKILRRKD                                                        189
```

```
gttcaaggtt acccatctca agtagcctag caacatttgc aacatcccaa tggccctgtc  60
cttttcttta ctgatggccg tgctggtgct cagctacaaa tccatctgtt ctctaggctg 120
tgatctgcct cagacccaca gcctgggtaa taggagggcc ttgatactcc tggcacaaat 180
gggaagaatc tctcctttct cctgctgaa ggacagacat gactttggac ttccccagga  240
ggagtttgat ggcaaccagt tccagaagac tcaagccatc tctgtcctcc atgagatgat 300
ccagcagacc ttcaatctct tcagcacaga ggactcatct gctgttggg aacagagcct  360
cctagaaaaa ttttccactg aactttacca gcaactgaat aacctggaag catgtgtgat 420
acaggaggtt gggatggaag agactcccct gatgaatgag gactccatcc tggctgtgag 480
gaaatacttc caaagaatca ctctttatct aacagagaag aaatacagcc cttgtgcctg 540
ggaggttgtc agagcagaaa tcatgagatc cctctctttt caacaaact tgcaaaaaat  600
attaaggagg aaggattgaa aactggttca acatggcaat gatcctgatt gactaataca 660
ttatctcaca ctttcatgag ttcctcaatt tcaaagactc acttctataa ccaccacgag 720
ttgaatcaaa attttcaaat gttttcagca gtgtaaagaa gcgtcgtgta tacctgtgca 780
ggcactagta ctttacagat gaccatgctg atgtctctgt tcatctattt atttaaatat 840
ttatttaatt attttaaga tttaaattat tttttatgt aatatcatgt gtacctttac   900
attgtggtga atgtaacaat atatgttctt catatttagc caatatatta atttcctttg 960
tcattaaatt tttactatac                                             980
```

GenBank Acc. No. M25460

```
MTNKCLLQIA LLLCFSTTAL SMSYNLLGFL QRSSNCQCQK LLWQLNGRLE YCLKDRRNFD  60
IPEEIKQLQQ FQKEDAAVTI YEMLQNIFAI FRQDSSSTGW NETIVENLLA NVYHQRNHLK 120
TVLEEKLEKE DFTRGKRMSS LHLKRYYGRI LHYLKAKEDS HCAWTIVRVE ILRNFYVINR 180
LTGYLRN                                                          187
```

```
gagtctaact gcaacctttc gaagcctttg ctctggcaca acaggtagta ggcgacactg  60
gtcgtgttgt tgacatgacc aacaagtgtc tcctccaaat tgctctcctg ttgtgcttct 120
ccacgacagc tctttccatg agctacaact tgcttggatt cctacaaaga agcagcaatt 180
gtcagtgtca gaagctcctg tggcaattga atgggaggct gaatactgc ctcaaggaca  240
ggaggaactt tgacatccct gaggagatta agcagctgca gcagttccag aaggaggacg 300
ccgcagtgac catctatgag atgctccaga acatctttgc tattttcaga caagattcat 360
cgagcactgg ctggaatgag actattgttg agaacctcct ggctaatgtc tatcatcaga 420
gaaaccatct gaagacagtc ctgaaagaaa aactggagaa agaagatttc accagggaa  480
aacgcatgag cagtctgcac ctgaaagat attatgggag gattctgcat tacctgaagg 540
ccaaggagga cagtcactgt gcctggacca tagtcagagt ggaaatccta aggaactttt 600
acgtcattaa cagacttaca ggttacctcc gaaactgaag atcctctagc ctgtgcctct 660
gggacgggac aattgcttca gcattcttc aaccagcaga tgctgtttaa gtgactgatg  720
gcgaatgtac tgcatatgaa aggacactag aagatttga aatttttatt aaattatgag  780
gtattttat ttatttaaat tttatttgg aaataaatt attttggtg caaaagtc       838
```

Fig. 7A

GenBank Acc. No. X13274

```
MKYTSYILAF QLCIVLGSLG CYCQDPYVKE AENLKKYFNA GHSDVADNGT LFLGILKNWK  60
EESDRKIMQS QIVSFYFKLF KNFKDDQSIQ KSVETIKEDM NVKFFNSNKK KRDDFEKLTN 120
YSVTDLNVQR KAIHELIQVM AELSPAAKTG KRKRSQMLFQ GRRASQ             166 tgaagatcag ctattagaag agaaagatca gttaagtcct ttggacctga tcagcttgat   60
acaagaacta ctgatttcaa cttctttggc ttaattctct cggaaacgat gaaatataca  120
agttatatct tggcttttca gctctgcatc gttttgggtt ctcttggctg ttactgccag  180
gacccatatg taaaagaagc agaaaacctt aagaaatatt ttaatgcagg tcattcagat  240
gtagcggata atggaactct ttcttaggc attttgaaga attggaaaga ggagagtgac  300
agaaaaataa tgcagagcca aattgtctcc ttttacttca aacttttaa aaactttaaa  360
gatgaccaga gcatccaaaa gagtgtggag accatcaagg aagacatgaa tgtcaagttt  420
ttcaatagca acaaaaagaa acgagatgac ttcgaaaagc tgactaatta ttcggtaact  480
gacttgaatg tccaacgcaa agcaatacat gaactcatcc aagtgatggc tgaactgtcg  540
ccagcagcta aacagggaa gcgaaaaagg agtcagatgc tgtttcaagg tcgaagagca  600
tcccagtaat ggttgtcctg cctgcaatat tgaatttta aatctaaatc tatttattaa  660
tatttaacat tatttatatg gggaatatat ttttagactc atcaatcaaa taagtattta  720
taatagcaac ttttgtgtaa tgaaaatgaa tatctattaa tatatgtatt atttataatt  780
cctatatcct gtgactgtct cacttaatcc tttgttttct gactaattag gcaaggctat  840
gtgattacaa ggctttatct caggggccaa ctaggcagcc aacctaagca agatcccatg  900
ggttgtgtgt ttatttcact tgatgataca atgaacactt ataagtgaag tgatactatc  960
cagttactgc cggtttgaaa atatgcctgc aatctgagcc agtgctttaa tggcatgtca  980
gacagaactt gaatgtgtca ggtgaccctg atgaaaacat agcatctcag gagatttcat 1040
gcctggtgct tccaaatatt gttgacaact gtgactgtac ccaaatggaa agtaactcat 1100
ttgttaaaat tatcaatatc taatatatat gaataaagtg taagttcaca act       1153
```

GenBank Acc. No. XM_071048

```
MIIKHFFGTV LVLLASTTIF SLDLKLIIFQ QRQVNQESLK LLNKLQTLSI QQCLPHRKNF  60
LLPQKSLSPQ QYQKGHTLAI LHEMLQQIFS LFRANISLDG WEENHTEKFL IQLHQQLEYL 120
EALMGLEAEK LSGTLGSDNL RLQVKMYFRR IHDYLENQDY STCAWAIVQV EISRCLFFVF 180
SLTEKLSKQG RPLNDMKQEL TTEFRSPREG EVKCT                           225 atgattatca agcacttctt tggaactgtg ttggtgctgc tggcctctac cactatcttc   60
tctctagatt tgaaactgat tatcttccag caaagacaag tgaatcaaga agtttaaaa  120
ctcttgaata gttgcaaac cttgtcaatt cagcagtgtc taccacacag gaaaaacttt  180
ctgcttcctc agaagtcttt gagtcctcag cagtaccaaa aggacacac tctggccatt  240
ctccatgaga tgcttcagca gatcttcagc ctcttcaggg caaatattc tctggatggt  300
tgggaggaaa accacacgga gaaattcctc attcaacttc atcaacagct agaatcccta  360
gaagcactca tgggactgga agcagagaag ctaagtggta ctttgggtag tgataacctt  420
agattacaag ttaaaatgta cttccgaagg atccatgatt acctggaaaa ccaggactac  480
agcacctgtg cctgggccat tgtccaagta gaaatcagcc gatgtctgtt ctttgtgttc  540
agcctcacag aaaaactgag caaacaagga agacccttga cgacatgaa gcaagagctt  600
actagagt ttagaagccc gagggaagga agttaaat gtacatag                 648
```

Fig. 7B

GenBank Acc. No. NM_002177

MALLFPLLAA LVMTSYSPVG SLGCDLPQNH GLLSRNTLVL LHQMRRISPF LCLKDRRDFR
FPQEMVKGSQ LQKAHVMSVL HEMLQQIFSL FHTERSSAAW NMTLLDQLHT GLHQQLQHLE
TCLLQVVGEG ESAGAISSPA LTLRRYFQGI RVYLKEKKYS DCAWEVVRME IMKSLFLSTN
MQERLRSKDR DLGSS

```
gatctggtaa acctgaagca aatatagaaa cctatagggc ctgacttcct acataaagta    60
aggagggtaa aaatggaggc tagaataagg gttaaaattt tgcttctaga acagagaaaa   120
tgatttttt  catatatata tgaatatata ttatatatac acatatatac atatattcac   180
tatagtgtgt atacataaat ataatatata tatattgtta gtgtagtgtg tgtctgatta   240
tttacatgca tatagtatat acacttatga ctttagtacc cagacgtttt tcatttgatt   300
aagcattcat ttgtattgac acagctgaag tttactggag tttagctgaa gtctaatgca   360
aaattaatag attgttgtca tcctcttaag gtcataggga aacacacaa atgaaaacag    420
taaaagaaac tgaaagtaca gagaaatgtt cagaaaatga aaccatgtg tttcctatta    480
aaagccatgc atacaagcaa tgtcttcaga aaacctaggg tccaaggtta agccatatcc   540
cagctcagta aagccaggag catcctcatt tcccaatggc cctcctgttc cctctactgg   600
cagccctagt gatgaccagc tatagccctg ttggatctct gggctgtgat ctgcctcaga   660
accatggcct acttagcagg aacaccttgg tgcttctgca ccaaatgagg agaatctccc   720
ctttcttgtg tctcaaggac agaagagact tcaggttccc ccaggagatg gtaaaaggga   780
gccagttgca gaaggccat  gtcatgtctg tcctccatga gatgctgcag cagatcttca   840
gcctcttcca cacagagcgc tcctctgctg cctggaacat gaccctccta gaccaactcc   900
acactggact tcatcagcaa ctgcaacacc tggagcctg cttgctgcag gtagtgggag    960
aaggagaatc tgctggggca attagcagcc ctgcactgac cttgaggagg tacttccagg   980
gaatccgtgt ctacctgaaa gagaagaaat acagcgactg tgcctgggaa gttgtcagaa  1040
tggaaatcat gaaatccttg ttcttatcaa caaacatgca agaaagactg agaagtaaag  1100
atagagacct gggctcatct tgaaatgatt ctcattgatt aatttgccat ataacacttg  1160
cacatgtgac tctggtcaat tcaaaagact cttatttcgg ctttaatcac agaattgact  1220
gaattagttc tgcaaatact ttgtcggtat attaagccag tatatgttaa aaagacttag  1280
gttcagggc  atcagtccct aagatgttat ttattttac tcatttattt attcttacat   1340
tttatcatat ttatactatt tatattctta taacaaat gtttgccttt acattgtatt   1400
aagataacaa aacatgttca gctttccatt tggttaaata ttgtattttg ttatttatta  1460
aattattttc aaac                                                    1474
```

Vaccinia virus interferon gamma receptor (B8R) gene (GenBank Acc. No. AF016273)

Amino acid sequence

MRYIIILAVLFINSIHAKITSYKFESVNFDSKIEWTGDGLYNISLKNYGIKTWQTMYTNVPE
GTYDISAFPKNDFVSFWVKFEQGDYKVEEYCTGPPTVTLTEYDDHPYATRGSKKIPIYKR
GDMCDIYLLYTANFTFGDSKEPVPYDIDDYDCTSTGCSIDFVTTEKVCVTAQGATEGFLE
KITPWSSKVCLTPKKSVYTCAIRSKEDVPNFKDKMARVIKRKFN

Nucleotide sequence attcaacgca gaggtcacac gtgtagaata tctaccaaat tatcatgcca ttatgataag taccettata ttcacaaata tgatggtgat
gagcgacaat attctattac tgcagaggga aaatgctata aaggaataaa atatgaaata agtatgatca acgatgatac tctattgaga
aaacatactc ttaaaattgg atctacttat atatttgatc gtcatggaca tagtaataca tattattcaa aatatgattt ttaaaaattt
aaaatatatt atcacttcag tgacagtagt caaataacaa acaacaccat gagatatatt ataattctcg cagttttgtt cattaatagt
atacacgcta aaataactag ttataagttt gaatccgtca attttgattc caaaattgaa tggactgggg atggtctata caatatatcc
cttaaaaatt atggcatcaa gacgtggcaa acaatgtata caaatgtacc agaaggaaca tacgacatat ccgcatttcc
aaagaatgat ttcgtatctt tctgggttaa atttgaacaa ggcgattata aagtggaaga gtattgtacg ggaccaccga ctgtaacatt
aactgaatac gacgaccatc cgtatgctac tagaggtagc aaaaagattc ctatttacaa acgcggtgac atgtgtgata tctacttgtt
gtatacggct aacttcacat tcggagattc taaagaacca gtaccatatg atatcgatga ctacgattgc acgtctacag gttgcagcat
agactttgtc acaacagaaa aagtgtgcgt gacagcacag ggagccacag aagggtttct cgaaaaaatt actccatgga
gttcgaaagt atgtctgaca cctaaaaaga gtgtatatac atgcgcaatt agatccaaag aagatgttcc caatttcaag gacaaaatgg
ccagagttat caagagaaaa tttaactaaa tttctcggta gcacatcaaa tgatgttacc actttcttta gcatgcttaa cttgactaaa
tattcataac taatttttat taatgataca aaaacgaaat aaaactgcat attatacact ggttaacgcc cttataggct ctaaccattt
tcaagatgag gtccctgatt atagtccttc tgttcccctc tatcatctac tccatgtcta ttagacgatg tgagaagact gaagaggaaa
catggggatt gaaaataggg ttgtgtataa ttgccaaaga tttctatccc gaaagaactg attgcagtgt tcatctccca actgcaagtg
aag

Fig. 8B

Vaccinia B18R-α/β binding proteins (GenBank Acc. No. A19579)

Amino acid sequence

MTMKMMVHIYFVSLLLLLFHSYAIDIENEITEFFNKMRDTLPAKDSKWLNPACMFGGTM
NDIAALGEPFSAKCPPIEDSLLSHRYKDYVVKWERLEKNRRRQVSNKRVKHGDLWIANY
TSKFSNRRYLCTVTTKNGDCVQGIVRSHIRKPPSCIPKTYELGTHDKYGIDLYCGILYAKH
YNNITWYKDNKEINIDDIKYSQTGKELIIHNPELEDSGRYDCYVHYDDVRIKNDIVVSRCK
ILTVIPSQDHRFKLILDPKINVTIGEPANITCTAVSTSLLIDDVLIEWENPSGWLIGFDFDVYS
VLTSRGGITEATLYFENVTEEYIGNTYKCR GHNYYFEKTLTTTVVLE

Nucleotide sequence gacaattaac gatctttata atatatcgta tccacctacc aaagtatagt tgtatttttc tcatgcgatg tgtgtaaaaa aactgatatt
atataaatat tttagtgccg tataataaag atgacgatga aaatgatggt acatatatat ttcgtatcat tattgttatt gctattccac
agttacgcca tagacatcga aaatgaaatc acagaattct tcaataaaat gagagatact ctaccagcta aagactctaa atggttgaat
ccagcatgta tgttcggagg cacaatgaat gatatagccg ctctaggaga gccattcagc gcaaagtgtc ctcctattga
agacagtctt ttatcgcaca gatataaaga ctatgtggtt aaatgggaaa ggctagaaaa aaatagacgg cgacaggttt
ctaataaacg tgttaaacat ggtgatttat ggatagccaa ctatacatct aaattcagta accgtaggta tttgtgcacc gtaactacaa
agaatggtga ctgtgttcag ggtatagtta gatctcatat tagaaaacct ccttcatgca ttccaaaaac atatgaacta ggtactcatg
ataagtatgg catagactta tactgtggaa ttctttacgc aaaacattat aataatataa cttggtataa agataataag gaaattaata
tcgacgacat taagtattca caaacgggaa aggaattaat tattcataat ccagagttag aagatagcgg aagatacgac tgttacgttc
attacgacga cgttagaatc aagaatgata tcgtagtatc aagatgtaaa atacttacgg ttataccgtc acaagaccac aggtttaaac
taatactaga tccaaaaatc aacgtaacga taggagaacc tgccaatata acatgcactg ctgtgtcaac gtcattattg attgacgatg
tactgattga atgggaaaat ccatccggat ggcttatagg attcgatttt gatgtatact ctgttttaac tagtagaggc ggtattaccg
aggcgaccct gtactttgaa aatgttactg aagaatatat aggtaataca tataaatgtc gtggacacaa ctattatttt gaaaaaaccc
ttacaactac agtagtattg gagtaaaatat acaatgcatt tttatataca ttactgaata attattatta ttattatat cgtatttgtg
ctataacgcg actatctagg tatttgtatc tcaccgatag agaacatata aat

SEQUENCE LISTING

<160> NUMBER OF SEQ ID NOS: 22

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atggctctcc tctttctcct a                                              21

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tctagaacct tttatactgc tattgaa                                        27

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tctagatggt gtgcagtgtc ggagc                                          25

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgtacggaaa gtgcaggctt ccag                                           24

-continued

```
<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
atgagatata ttataattc                                                    19

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcattagtta aattttctct tg                                                22

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agttacgcca tagacatcga a                                                 21

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcattactcc aatactactg tagt                                              24

<210> SEQ ID NO 9
<211> LENGTH: 189
<212> TYPE: PRT
<213> ORGANISM: Homo sapiens

<400> SEQUENCE: 9

Met Ala Leu Ser Phe Ser Leu Leu Met Ala Val Leu Val Leu Ser Tyr
  1               5                  10                  15

Lys Ser Ile Cys Ser Leu Gly Cys Asp Leu Pro Gln Thr His Ser Leu
             20                  25                  30

Gly Asn Arg Arg Ala Leu Ile Leu Leu Ala Gln Met Gly Arg Ile Ser
         35                  40                  45

Pro Phe Ser Cys Leu Lys Asp Arg His Asp Phe Gly Leu Pro Gln Glu
     50                  55                  60

Glu Phe Asp Gly Asn Gln Phe Gln Lys Thr Gln Ala Ile Ser Val Leu
 65                  70                  75                  80

His Glu Met Ile Gln Gln Thr Phe Asn Leu Phe Ser Thr Glu Asp Ser
                 85                  90                  95

Ser Ala Ala Trp Glu Gln Ser Leu Leu Glu Lys Phe Ser Thr Glu Leu
            100                 105                 110
```

Tyr Gln Gln Leu Asn Asn Leu Glu Ala Cys Val Ile Gln Glu Val Gly
            115                 120                 125

Met Glu Glu Thr Pro Leu Met Asn Glu Asp Ser Ile Leu Ala Val Arg
        130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Ile Leu Arg Arg Lys Asp
            180                 185

<210> SEQ ID NO 10
<211> LENGTH: 980
<212> TYPE: DNA
<213> ORGANISM: Homo sapiens

<400> SEQUENCE: 10
gttcaaggtt acccatctca agtagcctag caacatttgc aacatcccaa tggccctgtc      60
cttttcttta ctgatggccg tgctggtgct cagctacaaa tccatctgtt ctctaggctg     120
tgatctgcct cagacccaca gcctgggtaa taggagggcc ttgatactcc tggcacaaat     180
gggaagaatc tctcctttct cctgcctgaa ggacagacat gactttggac ttccccagga     240
ggagtttgat ggcaaccagt tccagaagac tcaagccatc tctgtcctcc atgagatgat     300
ccagcagacc ttcaatctct tcagcacaga ggactcatct gctgcttggg aacagagcct     360
cctagaaaaa ttttccactg aactttacca gcaactgaat aacctggaag catgtgtgat     420
acaggaggtt gggatggaag agactccct gatgaatgag gactccatcc tggctgtgag     480
gaaatacttc caaagaatca ctctttatct aacagagaag aaatacagcc cttgtgcctg     540
ggaggttgtc agagcagaaa tcatgagatc cctctctttt tcaacaaact tgcaaaaaat     600
attaaggagg aaggattgaa aactggttca acatggcaat gatcctgatt gactaataca     660
ttatctcaca ctttcatgag ttcctcaatt tcaaagactc acttctataa ccaccacgag     720
ttgaatcaaa attttcaaat gttttcagca gtgtaaagaa gcgtcgtgta tacctgtgca     780
ggcactagta ctttacagat gaccatgctg atgtctctgt tcatctattt atttaaatat     840
ttatttaatt atttttaaga tttaaattat tttttatgt aatatcatgt gtacctttac     900
attgtggtga atgtaacaat atatgttctt catatttagc caatatatta atttcctttt     960
tcattaaatt tttactatac                                                 980

<210> SEQ ID NO 11
<211> LENGTH: 187
<212> TYPE: PRT
<213> ORGANISM: Homo sapiens

<400> SEQUENCE: 11

Met Thr Asn Lys Cys Leu Leu Gln Ile Ala Leu Leu Leu Cys Phe Ser
  1               5                  10                  15

Thr Thr Ala Leu Ser Met Ser Tyr Asn Leu Leu Gly Phe Leu Gln Arg
             20                  25                  30

Ser Ser Asn Cys Gln Cys Gln Lys Leu Leu Trp Gln Leu Asn Gly Arg
         35                  40                  45

Leu Glu Tyr Cys Leu Lys Asp Arg Arg Asn Phe Asp Ile Pro Glu Glu
     50                  55                  60

Ile Lys Gln Leu Gln Gln Phe Gln Lys Glu Asp Ala Ala Val Thr Ile

```
                65                   70                  75                   80
Tyr Glu Met Leu Gln Asn Ile Phe Ala Ile Phe Arg Gln Asp Ser Ser
                        85                  90                  95

Ser Thr Gly Trp Asn Glu Thr Ile Val Glu Asn Leu Leu Ala Asn Val
                100                 105                 110

Tyr His Gln Arg Asn His Leu Lys Thr Val Leu Glu Glu Lys Leu Glu
            115                 120                 125

Lys Glu Asp Phe Thr Arg Gly Lys Arg Met Ser Ser Leu His Leu Lys
        130                 135                 140

Arg Tyr Tyr Gly Arg Ile Leu His Tyr Leu Lys Ala Lys Glu Asp Ser
145                 150                 155                 160

His Cys Ala Trp Thr Ile Val Arg Val Glu Ile Leu Arg Asn Phe Tyr
                165                 170                 175

Val Ile Asn Arg Leu Thr Gly Tyr Leu Arg Asn
                180                 185
```

<210> SEQ ID NO 12
<211> LENGTH: 838
<212> TYPE: DNA
<213> ORGANISM: Homo sapiens

<400> SEQUENCE: 12

```
gagtctaact gcaacctttc gaagcctttg ctctggcaca acaggtagta ggcgacactg    60
gtcgtgttgt tgacatgacc aacaagtgtc tcctccaaat tgctctcctg ttgtgcttct   120
ccacgacagc tctttccatg agctacaact tgcttggatt cctacaaaga agcagcaatt   180
gtcagtgtca gaagctcctg tggcaattga atgggaggct tgaatactgc ctcaaggaca   240
ggaggaactt tgacatccct gaggagatta gcagctgca gcagttccag aaggaggacg   300
ccgcagtgac catctatgag atgctccaga acatctttgc tattttcaga caagattcat   360
cgagcactgg ctggaatgag actattgttg agaacctcct ggctaatgtc tatcatcaga   420
gaaaccatct gaagacagtc ctggaagaaa aactggagaa agaagatttc accaggggaa   480
aacgcatgag cagtctgcac ctgaaaagat attatgggag gattctgcat acctgaagg   540
ccaaggagga cagtcactgt gcctggacca tagtcagagt ggaaatccta aggaactttt   600
acgtcattaa cagacttaca ggttacctcc gaaactgaag atctcctagc ctgtgcctct   660
gggacgggac aattgcttca gcattcttc aaccagcaga tgctgtttaa gtgactgatg   720
gcgaatgtac tgcatatgaa aggacactag aagattttga aatttttatt aaattatgag   780
gtatttttat ttatttaaat tttatttgg aaaataaatt attttggtg caaaagtc     838
```

<210> SEQ ID NO 13
<211> LENGTH: 166
<212> TYPE: PRT
<213> ORGANISM: Homo sapiens

<400> SEQUENCE: 13

```
Met Lys Tyr Thr Ser Tyr Ile Leu Ala Phe Gln Leu Cys Ile Val Leu
1                   5                   10                  15

Gly Ser Leu Gly Cys Tyr Cys Gln Asp Pro Tyr Val Lys Glu Ala Glu
                20                  25                  30

Asn Leu Lys Lys Tyr Phe Asn Ala Gly His Ser Asp Val Ala Asp Asn
            35                  40                  45

Gly Thr Leu Phe Leu Gly Ile Leu Lys Asn Trp Lys Glu Glu Ser Asp
        50                  55                  60
```

```
Arg Lys Ile Met Gln Ser Gln Ile Val Ser Phe Tyr Phe Lys Leu Phe
 65                  70                  75                  80

Lys Asn Phe Lys Asp Asp Gln Ser Ile Gln Lys Ser Val Glu Thr Ile
                 85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Gln
145                 150                 155                 160

Gly Arg Arg Ala Ser Gln
                165

<210> SEQ ID NO 14
<211> LENGTH: 1193
<212> TYPE: DNA
<213> ORGANISM: Homo sapiens

<400> SEQUENCE: 14
tgaagatcag ctattagaag agaaagatca gttaagtcct ttggacctga tcagcttgat      60
acaagaacta ctgatttcaa cttctttggc ttaattctct cggaaacgat gaaatataca     120
agttatatct tggcttttca gctctgcatc gttttgggtt ctcttggctg ttactgccag     180
gacccatatg taaaagaagc agaaaacctt aagaaatatt ttaatgcagg tcattcagat     240
gtagcggata atggaactct tttcttaggc attttgaaga attggaaaga ggagagtgac     300
agaaaaataa tgcagagcca aattgtctcc ttttacttca actttttaa aaactttaaa      360 gatgaccaga gcatccaaaa gagtgtggag accatcaagg aagacatgaa tgtcaagttt     420
ttcaatagca caaaaagaa acgagatgac ttcgaaaagc tgactaatta ttcggtaact      480
gacttgaatg tccaacgcaa agcaatacat gaactcatcc aagtgatggc tgaactgtcg     540
ccagcagcta aaacagggaa gcgaaaaagg agtcagatgc tgtttcaagg tcgaagagca     600
tcccagtaat ggttgtcctg cctgcaatat ttgaatttta atctaaatc tatttattaa      660 tatttaacat tatttatatg gggaatatat ttttagactc atcaatcaaa taagtattta     720
taatagcaac ttttgtgtaa tgaaaatgaa tatctattaa tatatgtatt atttataatt     780
cctatatcct gtgactgtct cacttaatcc tttgttttct gactaattag gcaaggctat     840
gtgattacaa ggctttatct caggggccaa ctaggcagcc aacctaagca agatccccatg    900 ggttgtgtgt ttatttcact tgatgataca atgaacactt ataagtgaag tgatactatc     960
cagttactgc cggtttgaaa atatgcctgc aatctgagcc agtgctttaa tggcatgtca    1020
gacagaactt gaatgtgtca ggtgaccctg atgaaaacat agcatctcag gagatttcat   1080
gcctggtgct tccaaatatt gttgacaact gtgactgtac ccaaatggaa agtaactcat   1140
ttgttaaaat tatcaatatc taatatatat gaataaagtg taagttcaca act          1193

<210> SEQ ID NO 15
<211> LENGTH: 215
<212> TYPE: PRT
<213> ORGANISM: Homo sapiens

<400> SEQUENCE: 15

Met Ile Ile Lys His Phe Phe Gly Thr Val Leu Val Leu Leu Ala Ser
 1               5                  10                  15
```

Thr Thr Ile Phe Ser Leu Asp Leu Lys Leu Ile Ile Phe Gln Gln Arg
                20                  25                  30

Gln Val Asn Gln Glu Ser Leu Lys Leu Leu Asn Lys Leu Gln Thr Leu
             35                  40                  45

Ser Ile Gln Gln Cys Leu Pro His Arg Lys Asn Phe Leu Leu Pro Gln
         50                  55                  60

Lys Ser Leu Ser Pro Gln Gln Tyr Gln Lys Gly His Thr Leu Ala Ile
 65                  70                  75                  80

Leu His Glu Met Leu Gln Gln Ile Phe Ser Leu Phe Arg Ala Asn Ile
                 85                  90                  95

Ser Leu Asp Gly Trp Glu Glu Asn His Thr Glu Lys Phe Leu Ile Gln
            100                 105                 110

Leu His Gln Gln Leu Glu Tyr Leu Glu Ala Leu Met Gly Leu Glu Ala
         115                 120                 125

Glu Lys Leu Ser Gly Thr Leu Gly Ser Asp Asn Leu Arg Leu Gln Val
130                 135                 140

Lys Met Tyr Phe Arg Arg Ile His Asp Tyr Leu Glu Asn Gln Asp Tyr
145                 150                 155                 160

Ser Thr Cys Ala Trp Ala Ile Val Gln Val Glu Ile Ser Arg Cys Leu
                165                 170                 175

Phe Phe Val Phe Ser Leu Thr Glu Lys Leu Ser Lys Gln Gly Arg Pro
            180                 185                 190

Leu Asn Asp Met Lys Gln Glu Leu Thr Thr Glu Phe Arg Ser Pro Arg
         195                 200                 205

Glu Gly Glu Val Lys Cys Thr
    210                 215

<210> SEQ ID NO 16
<211> LENGTH: 648
<212> TYPE: DNA
<213> ORGANISM: Homo sapiens

<400> SEQUENCE: 16
atgattatca agcacttctt tggaactgtg ttggtgctgc tggcctctac cactatcttc      60
tctctagatt tgaaactgat tatcttccag caaagacaag tgaatcaaga aagtttaaaa     120
ctcttgaata agttgcaaac cttgtcaatt cagcagtgtc taccacacag gaaaaacttt     180
ctgcttcctc agaagtcttt gagtcctcag cagtaccaaa aaggacacac tctggccatt     240
ctccatgaga tgcttcagca gatcttcagc tcttcagggg caaatatttc tctggatggt     300
tgggaggaaa accacacgga gaaattcctc attcaacttc atcaacagct agaataccta     360
gaagcactca tgggactgga agcagagaag ctaagtggta ctttgggtag tgataacctt     420
agattacaag ttaaaatgta cttccgaagg atccatgatt acctggaaaa ccaggactac     480
agcacctgtg cctgggccat tgtccaagta gaaatcagcc gatgtctgtt ctttgtgttc     540
agtctcacag aaaaactgag caaacaagga agacccttga cgacatgaa gcaagagctt      600 actacagagt ttagaagccc gagggaagga gaagttaaat gtacatag                 648

<210> SEQ ID NO 17
<211> LENGTH: 195
<212> TYPE: PRT
<213> ORGANISM: Homo sapiens

<400> SEQUENCE: 17

Met Ala Leu Leu Phe Pro Leu Leu Ala Ala Leu Val Met Thr Ser Tyr

```
                 1               5              10              15
        Ser Pro Val Gly Ser Leu Gly Cys Asp Leu Pro Gln Asn His Gly Leu
                         20                  25                  30

Leu Ser Arg Asn Thr Leu Val Leu Leu His Gln Met Arg Ile Ser
                     35                  40                  45

Pro Phe Leu Cys Leu Lys Asp Arg Arg Asp Phe Arg Phe Pro Gln Glu
                         50                  55                  60

Met Val Lys Gly Ser Gln Leu Gln Lys Ala His Val Met Ser Val Leu
         65                  70                  75                  80

His Glu Met Leu Gln Gln Ile Phe Ser Leu Phe His Thr Glu Arg Ser
                         85                  90                  95

Ser Ala Ala Trp Asn Met Thr Leu Leu Asp Gln Leu His Thr Gly Leu
                         100                 105                 110

His Gln Gln Leu Gln His Leu Glu Thr Cys Leu Leu Gln Val Val Gly
                         115                 120                 125

Glu Gly Glu Ser Ala Gly Ala Ile Ser Ser Pro Ala Leu Thr Leu Arg
                         130                 135                 140

Arg Tyr Phe Gln Gly Ile Arg Val Tyr Leu Lys Glu Lys Lys Tyr Ser
        145                 150                 155                 160

Asp Cys Ala Trp Glu Val Val Arg Met Glu Ile Met Lys Ser Leu Phe
                         165                 170                 175

Leu Ser Thr Asn Met Gln Glu Arg Leu Arg Ser Lys Asp Arg Asp Leu
                         180                 185                 190

Gly Ser Ser
                195

<210> SEQ ID NO 18
<211> LENGTH: 1514
<212> TYPE: DNA
<213> ORGANISM: Homo sapiens

<400> SEQUENCE: 18
gatctggtaa acctgaagca aatatagaaa cctatagggc ctgacttcct acataaagta      60
aggagggtaa aaatggaggc tagaataagg gttaaaattt tgcttctaga acagagaaaa    120
tgatttttttt catatatata tgaatatata ttatatatac acatatatac atatattcac    180
tatagtgtgt atacataaat ataatatata tatattgtta gtgtagtgtg tgtctgatta    240
tttacatgca tatagtatat acacttatga ctttagtacc cagacgtttt tcatttgatt    300
aagcattcat ttgtattgac acagctgaag tttactggag tttagctgaa gtctaatgca    360
aaattaatag attgttgtca tcctcttaag gtcatatggga gaacacacaa atgaaaacag    420
taaaagaaac tgaaagtaca gagaaatgtt cagaaaatga aaaccatgtg tttcctatta    480
aaagccatgc atacaagcaa tgtcttcaga aaacctaggg tccaaggtta agccatatcc    540
cagctcagta aagccaggag catcctcatt tcccaatggc cctcctgttc cctctactgg    600
cagccctagt gatgaccagc tatagccctg ttggatctct gggctgtgat ctgcctcaga    660
accatggcct acttagcagg aacaccttgg tgcttctgca ccaaatgagg agaatctccc    720
ctttcttgtg tctcaaggac agaagagact tcaggttccc ccaggagatg gtaaaaggga    780
gccagttgca gaaggcccat gtcatgtctg tcctccatga gatgctgcag cagatcttca    840
gcctcttcca cacagagcgc tcctctgctg cctggaacat gaccctccta gaccaactcc    900
acactggact tcatcagcaa ctgcaacacc tggagacctg cttgctgcag gtagtgggag    960
aaggagaatc tgctggggca attagcagcc ctgcactgac cttgaggagg tacttccagg   1020
```

```
gaatccgtgt ctacctgaaa gagaagaaat acagcgactg tgcctgggaa gttgtcagaa    1080
tggaaatcat gaaatccttg ttcttatcaa caaacatgca agaaagactg agaagtaaag    1140
atagagacct gggctcatct tgaaatgatt ctcattgatt aatttgccat ataacacttg    1200
cacatgtgac tctggtcaat tcaaaagact cttatttcgg ctttaatcac agaattgact    1260
gaattagttc tgcaaatact ttgtcggtat attaagccag tatatgttaa aaagacttag    1320
gttcaggggc atcagtccct aagatgttat ttattttac tcatttattt attcttacat     1380
tttatcatat ttatactatt tatattctta tataacaaat gtttgccttt acattgtatt    1440
aagataacaa aacatgttca gctttccatt tggttaaata ttgtattttg ttatttatta    1500
aattattttc aaac                                                     1514
```

```
<210> SEQ ID NO 19
<211> LENGTH: 226
<212> TYPE: PRT
<213> ORGANISM: Vaccinia virus

<400> SEQUENCE: 19
```

Met Arg Tyr Ile Ile Ile Leu Ala Val Leu Phe Ile Asn Ser Ile His
1               5                   10                  15

Ala Lys Ile Thr Ser Tyr Lys Phe Glu Ser Val Asn Phe Asp Ser Lys
            20                  25                  30

Ile Glu Trp Thr Gly Asp Gly Leu Tyr Asn Ile Ser Leu Lys Asn Tyr
        35                  40                  45

Gly Ile Lys Thr Trp Gln Thr Met Tyr Thr Asn Val Pro Glu Gly Thr
    50                  55                  60

Tyr Asp Ile Ser Ala Phe Pro Lys Asn Asp Phe Val Ser Phe Trp Val
65                  70                  75                  80

Lys Phe Glu Gln Gly Asp Tyr Lys Val Glu Glu Tyr Cys Thr Gly Pro
                85                  90                  95

Pro Thr Val Thr Leu Thr Glu Tyr Asp Asp His Pro Tyr Ala Thr Arg
            100                 105                 110

Gly Ser Lys Lys Ile Pro Ile Tyr Lys Arg Gly Asp Met Cys Asp Ile
        115                 120                 125

Tyr Leu Leu Tyr Thr Ala Asn Phe Thr Phe Gly Asp Ser Lys Glu Pro
    130                 135                 140

Val Pro Tyr Asp Ile Asp Asp Tyr Asp Cys Thr Ser Thr Gly Cys Ser
145                 150                 155                 160

Ile Asp Phe Val Thr Thr Glu Lys Val Cys Val Thr Ala Gln Gly Ala
                165                 170                 175

Thr Glu Gly Phe Leu Glu Lys Ile Thr Pro Trp Ser Ser Lys Val Cys
            180                 185                 190

Leu Thr Pro Lys Lys Ser Val Tyr Thr Cys Ala Ile Arg Ser Lys Glu
        195                 200                 205

Asp Val Pro Asn Phe Lys Asp Lys Met Ala Arg Val Ile Lys Arg Lys
    210                 215                 220

Phe Asn
225

```
<210> SEQ ID NO 20
<211> LENGTH: 1333
<212> TYPE: DNA
<213> ORGANISM: Vaccinia virus

<400> SEQUENCE: 20
```

-continued

```
attcaacgca gaggtcacac gtgtagaata tctaccaaat tatcatgcca ttatgataag      60 taccettata ttcacaaata tgatggtgat gagcgacaat attctattac tgcagaggga     120
aaatgctata aaggaataaa atatgaaata agtatgatca acgatgatac tctattgaga     180
aaacatactc ttaaaattgg atctacttat atatttgatc gtcatggaca tagtaataca     240
tattattcaa aatatgattt ttaaaaattt aaaatatatt atcacttcag tgacagtagt     300
caaataacaa acaacaccat gagatatatt ataattctcg cagttttgtt cattaatagt     360
atacacgcta aaataactag ttataagttt gaatccgtca attttgattc caaaattgaa     420
tggactgggg atggtctata caatatatcc cttaaaaatt atggcatcaa gacgtggcaa     480
acaatgtata caaatgtacc agaaggaaca tacgacatat ccgcatttcc aaagaatgat     540
ttcgtatctt tctgggttaa atttgaacaa ggcgattata aagtggaaga gtattgtacg     600
ggaccaccga ctgtaacatt aactgaatac gacgaccatc cgtatgctac tagaggtagc     660
aaaaagattc ctatttacaa acgcggtgac atgtgtgata tctacttgtt gtatacggct     720
aacttcacat tcggagattc taaagaacca gtaccatatg atatcgatga ctacgattgc     780
acgtctacag gttgcagcat agactttgtc acaacagaaa aagtgtgcgt gacagcacag     840
ggagccacag aagggtttct cgaaaaaatt actccatgga gttcgaaagt atgtctgaca     900
cctaaaaaga gtgtatatac atgcgcaatt agatccaaag aagatgttcc caatttcaag     960
gacaaaatgg ccagagttat caagagaaaa tttaactaaa tttctcggta gcacatcaaa    1020
tgatgttacc acttttctta gcatgcttaa cttgactaaa tattcataac taatttttat    1080
taatgataca aaaacgaaat aaaactgcat attatacact ggttaacgcc cttataggct    1140
ctaaccattt tcaagatgag gtccctgatt atagtccttc tgttcccctc tatcatctac    1200
tccatgtcta ttagacgatg tgagaagact gaagaggaaa catggggatt gaaaataggg    1260
ttgtgtataa ttgccaaaga tttctatccc gaaagaactg attgcagtgt tcatctccca    1320
actgcaagtg aag                                                        1333
```

<210> SEQ ID NO 21
<211> LENGTH: 351
<212> TYPE: PRT
<213> ORGANISM: Vaccinia virus

<400> SEQUENCE: 21

```
Met Thr Met Lys Met Met Val His Ile Tyr Phe Val Ser Leu Leu Leu
1               5                   10                  15

Leu Leu Phe His Ser Tyr Ala Ile Asp Ile Glu Asn Glu Ile Thr Glu
            20                  25                  30

Phe Phe Asn Lys Met Arg Asp Thr Leu Pro Ala Lys Asp Ser Lys Trp
        35                  40                  45

Leu Asn Pro Ala Cys Met Phe Gly Gly Thr Met Asn Asp Ile Ala Ala
    50                  55                  60

Leu Gly Glu Pro Phe Ser Ala Lys Cys Pro Pro Ile Glu Asp Ser Leu
65                  70                  75                  80

Leu Ser His Arg Tyr Lys Asp Tyr Val Val Lys Trp Glu Arg Leu Glu
                85                  90                  95

Lys Asn Arg Arg Arg Gln Val Ser Asn Lys Arg Val Lys His Gly Asp
            100                 105                 110

Leu Trp Ile Ala Asn Tyr Thr Ser Lys Phe Ser Asn Arg Arg Tyr Leu
        115                 120                 125
```

| | | | | | | | | | | | |
|---|---|---|---|---|---|---|---|---|---|---|---|
|Cys|Thr|Val|Thr|Thr|Lys|Asn|Gly|Asp|Cys|Val|Gln|Gly|Ile|Val|Arg|
| |130| | | |135| | | |140| | | | | | |

Ser His Ile Arg Lys Pro Pro Ser Cys Ile Pro Lys Thr Tyr Glu Leu
145                 150                 155                 160

Gly Thr His Asp Lys Tyr Gly Ile Asp Leu Tyr Cys Gly Ile Leu Tyr
                165                 170                 175

Ala Lys His Tyr Asn Asn Ile Thr Trp Tyr Lys Asp Asn Lys Glu Ile
            180                 185                 190

Asn Ile Asp Asp Ile Lys Tyr Ser Gln Thr Gly Lys Glu Leu Ile Ile
                195                 200                 205

His Asn Pro Glu Leu Glu Asp Ser Gly Arg Tyr Asp Cys Tyr Val His
    210                 215                 220

Tyr Asp Asp Val Arg Ile Lys Asn Asp Ile Val Val Ser Arg Cys Lys
225                 230                 235                 240

Ile Leu Thr Val Ile Pro Ser Gln Asp His Arg Phe Lys Leu Ile Leu
                245                 250                 255

Asp Pro Lys Ile Asn Val Thr Ile Gly Glu Pro Ala Asn Ile Thr Cys
            260                 265                 270

Thr Ala Val Ser Thr Ser Leu Leu Ile Asp Asp Val Leu Ile Glu Trp
    275                 280                 285

Glu Asn Pro Ser Gly Trp Leu Ile Gly Phe Asp Phe Asp Val Tyr Ser
290                 295                 300

Val Leu Thr Ser Arg Gly Gly Ile Thr Glu Ala Thr Leu Tyr Phe Glu
305                 310                 315                 320

Asn Val Thr Glu Glu Tyr Ile Gly Asn Thr Tyr Lys Cys Arg Gly His
                325                 330                 335

Asn Tyr Tyr Phe Glu Lys Thr Leu Thr Thr Thr Val Val Leu Glu
            340                 345                 350

<210> SEQ ID NO 22
<211> LENGTH: 1293
<212> TYPE: DNA
<213> ORGANISM: Vaccinia virus

<400> SEQUENCE: 22

```
gacaattaac gatctttata atatatcgta tccacctacc aaagtatagt tgtattttc    60
tcatgcgatg tgtgtaaaaa aactgatatt atataaatat tttagtgccg tataataag   120
atgacgatga aaatgatggt acatatatat ttcgtatcat tattgttatt gctattccac  180
agttacgcca tagacatcga aaatgaaatc acagaattct tcaataaaat gagagatact  240
ctaccagcta aagactctaa atggttgaat ccagcatgta tgttcggagg cacaatgaat  300
gatatagccg ctctaggaga gccattcagc gcaaagtgtc ctcctattga agacagtctt  360
ttatcgcaca gatataaaga ctatgtggtt aaatgggaaa ggctagaaaa aaatagacgg  420
cgacaggttt ctaataaacg tgttaaacat ggtgatttat ggatagccaa ctatacatct  480
aaattcagta accgtaggta tttgtgcacc gtaactacaa agaatggtga ctgtgttcag  540
ggtatagtta gatctcatat tagaaaacct ccttcatgca ttccaaaaac atatgaacta  600
ggtactcatg ataagtatgg catagactta tactgtggaa ttctttacgc aaaacattat  660
aataatataa cttggtataa agataataag gaaattaata tcgacgacat taagtattca  720
caaacgggaa aggaattaat tattcataat ccagagttag aagatagcgg aagatacgac  780
tgttacgttc attacgacga cgttagaatc aagaatgata tcgtagtatc aagatgtaaa  840
atacttacgg ttataccgtc acaagaccac aggtttaaac taatactaga tccaaaaatc  900
```

```
aacgtaacga taggagaacc tgccaatata acatgcactg ctgtgtcaac gtcattattg    960
attgacgatg tactgattga atgggaaaat ccatccggat ggcttatagg attcgatttt   1020
gatgtatact ctgttttaac tagtagaggc ggtattaccg aggcgacctt gtactttgaa   1080
aatgttactg aagaatatat aggtaataca tataaatgtc gtggacacaa ctattatttt   1140
gaaaaaaccc ttacaactac agtagtattg gagtaaatat acaatgcatt tttatataca   1200
ttactgaata attattatta ttatttatat cgtatttgtg ctataacgcg actatctagg   1260
tatttgtatc tcaccgatag agaacatata aat                                1293
```

INTERFERON ANTAGONISTS USEFUL FOR THE TREATMENT OF INTERFERON RELATED DISEASES

CROSS REFERENCE TO RELATED APPLICATIONS

This application is a divisional application of U.S. application Ser. No. 10/284,740, filed Oct. 31, 2002, now U.S. Pat. No. 7,285,526, issued Oct. 23, 2007, which is a continuation-in-part of U.S. application Ser. No. 09/845,260, filed Apr. 30, 2001, now abandoned, which is a continuation of U.S. application Ser. No. 09/067,398, filed Apr. 28, 1998, now abandoned, which is a continuation of U.S. application Ser. No. 08/502,519, filed Jul. 14, 1995, now U.S. Pat. No. 5,780,027, issued Jul. 14, 1998. The entire teaching of the above applications are incorporated herein by reference.

BACKGROUND

1. Field of the Invention

The present invention relates to a process for ameliorating or preventing diseases that are caused, in part, by an increased level of, and/or an abnormal responsivity to, interferon. Alzheimer's disease, HIV infection, Down syndrome, transplant rejection, autoimmune disease, and infant encephalitis are examples of such diseases. Specifically, the invention provides a method for treating subjects suffering from, or at risk for, such diseases by the administration of a pharmacological preparation of interferon binding proteins of mammalian and/or viral origin that antagonize interferon's action. This invention comprises compositions of interferon binding proteins that can inhibit the activity of interferon gamma plus interferon alpha such compositions along with their method of production and modification being described herein.

2. Background of the Invention

The Molecular Biology of Interferons and Interferon Receptors

Interferons are proteins that alter and regulate the transcription of genes within a cell by binding to interferon receptors on the regulated cell's surface and thus prevent viral replication within the cells. There are five types of interferons (IFN), which are designated α (formerly α1), ω (formerly α2), β, γ and τ. Mature human interferons are between 165 and 172 amino acids in length. In humans IFN-α and IFN-ω are encoded by multiple, closely related non-allelic genes. Additionally, there are pseudo-genes of IFN-α and IFN-ω. By contrast, IFN-β and IFN-γ are encoded by unique genes.

The interferons can be grouped into two types. IFN-γ is the sole type II interferon; all others are type I interferons. Type I and type II interferons differ in gene structure (type II interferon genes have three exons, type I one), chromosome location (in humans, type II is located on chromosome-12; the type I interferon genes are linked and on chromosome-9), and the types of tissues where they are produced (type I interferons are synthesized ubiquitously, type II by lymphocytes). Type I interferons competitively inhibit each others binding to cellular receptors, while type II interferon has a distinct receptor. Reviewed by Sen, G. C. & Lengyel, P., 1992, J. Biol. Chem. 267:5017-5020.

Although all type I interferons compete for binding to a common receptor or receptors, the effects of different type I interferons can be different. Pontzer, C. H., 1994, J. Interfer. Res. 14:133-41. Additionally, there appears to be several kinds of type I interferon receptor. For example, there is evidence that the type I interferon receptors of different cell types are different. Benoit, P., 1993, J. Immunol. 150:707. The number of genes encoding the type I interferon receptors is unknown: however, the genes appear to be linked to each other and to at least one gene encoding an IFN-γ receptor component as well. In humans, chromosome region 21q21.1-21.31 encodes all the genes needed for the receptor for type I interferon (Raziuddin, A., 1984, Proc. Natl. Acad. Sci. 81:5504-08; Soh, J., 1993, Proc. Natl. Acad. Sci. 90:8737-41; Soh, J., 1994, J. Biol. Chem. 269:18102-10) and at least one essential component of the type II interferon receptor (Jung, V., 1990, J. Biol. Chem. 265:1827-30).

It is becoming increasingly clear that the interferons have an important role in neuromodulation (Hori, T. et al., 1998, Neuroimmunomodulation 5:172-177; Dafny, N., 1998, Brain Res. Brain Res. Rev. 26:1-15) and neurodegeneracy (Blasko, I. et al., 2001, J. Neuroimmunol. 116:1-4). Of particular relevance is the observation of neuropathology associated with the overproduction of either IFN-α (Akwa, Y. et al., 1998, J. Immunol. 161:5016-5026) or IFN-γ (Corbin, J. G. et al., 1996, Mol Cell Neurosci. 7:354-370) in the transgenic mouse brain. Evidence has been presented in support of a role for IFN-α in neuromodulation (reviewed by Dafney (Dafny, N., 1998, Brain Res Brain Res Rev. 26:1-15)).

The potential role of IFN-γ in neurodegeneracy has only recently been recognized (Blasko, I. et al., 2001, J Neuroimmunol. 116:1-4). Evidence has been presented for a direct role for IFN-γ in neuron apoptosis of neurons in culture (Hallam, D. M. et al., 1998, Neurosci. Lett. 252:17-20) through the induction of neuron caspase activity (Hallam, D. M. et al., 2000, J. Neuroimmunol. 110:66-75).

The Biology of Interferon Action and Down Syndrome

The binding of interferons to their receptor, leads to a cascade post-translational modification to other proteins which are then transported to the nucleus where they regulate the transcription of genes by binding to specific nucleic acid sequences. The nucleic acid sequence which is characteristic of genes responsive to type I interferons is designated the Interferon Sensitive Response Element (ISRE). Reviewed Tanaka, T. & Taniguchi, T., 1992, Adv. Immunol. 52:263. Type-I interferons are synthesized in response to viral infection, except for IFN-τ which is constitutively produced in the placenta; Type II interferons are synthesized in response to antigen stimulation.

Interferons alter the rates of synthesis and the steady state levels of many cellular proteins. An overall effect of interferon is usually an inhibition of cellular proliferation.

The possibility that cells from subjects having Down syndrome may have abnormal responsivity to interferon was introduced by the discovery that a gene encoding an interferon inducible protein, which was subsequently identified as the type I interferon receptor, was located on chromosome-21. Tan Y. H. et al., 1974, J. Exp. Med. 137:317-330. This observation prompted comparisons of the response of diploid and trisomy-21 aneuploid cultured cells to interferon added to the culture medium. These studies have consistently shown an increased responsivity of trisomy-21 cells to interferon. Tan, Y. H. et al., 1974, Science 186:61-63; Maroun, L. E., 1979, J. Biochem. 179:221; Weil, J. et al., 1983, Hum. Genetics 65:108-111; reviewed Epstein, C. J., & Epstein, L. B., 8 LYMPHOKINES pp 277-301 (Academic Press, New York, 1983); Epstein, C. J. et al., 1987, ONCOLOGY AND IMMUNOLOGY OF DOW SYNDROME (Alan R. Liss, 1987). The publications of these studies have been accompanied by speculative conjectures that the altered responsivity to interferon played a role in the pathogenesis of lesions of Down syndrome. See, Maroun, L. E., 1980, J. Theoret. Biol. 86:603-606.

Down Syndrome and Animal Models of It

An animal model of Down syndrome has been constructed by use of the knowledge that human chromosome-21 is syntenic to mouse chromosome-16, i.e., that many of the genes present on each are homologs of each other. Mice having specified trisomies can be bred by use of parental mice having "Robertsonian" chromosomes, i.e., chromosomes that are essentially the centromeric fusion of two different murine chromosomes. A variety of such Robertsonian chromosomes have been identified, including at least two involving chromosome-16 and a second different chromosome: Rb(16.17) and Rb(6.16). Mice homozygous for any Robertsonian or combination of independent Robersonian chromosomes are euploid and fertile.

The intercross (F1) between an Rb(16.17) and an Rb(6.16) mouse is also fully diploid at each genetic locus, although errors in meiosis may cause reduced fertility. Note that in such an F1 both the maternal and paternal chromosome-16 are a part of a Robertsonian chromosome.

Because of meiotic errors the outcross between a mouse having both two different Robertsonian chromosome-16's and a non-Robertsonian mouse gives rise to a trisomy-16 conceptus in between 15% and 20% of cases. Gearhart, J. D. et al., 1986, Brain Res. Bull. 16:789-801; Gropp, A. et al., 1975, Cytogenet. Cell Genet. 14:42-62. The murine trisomy-16 fetuses develop to term but do not live beyond birth by more than a few hours.

Examination of the fetal trisomy-16 and the postpartum human trisomy-21 reveals a number of analogous or parallel lesions. For this reason, the murine trisomy-16 construct is considered to be an animal model of Down syndrome. Epstein, C. J., THE METABOLIC BASIS OF INHERITED DISEASE, 6TH ED. pp 291-326 (McGraw-Hill, New York, 1989); Epstein, C. J. et al., 1985, Ann. N.Y. Acad. Sci. 450: 157-168. Because a murine trisomy-16 fetus is not viable post partum, the opportunity to study the neurological pathology of the model has been limited. However, it is clear that in both human trisomy-21 and murine trisomy-16 there is an overall reduction in fetal size and particularly in the development of the fetal brain. Epstein, C. J., THE CONSEQUENCES OF CHROMOSOME IMBALANCE: PRINCIPLES, MECHANISMS AND MODELS (Cambridge University Press, New York, 1986). Further insights into the effects of marine trisomy-16 have been obtained by the formation of Ts16←→2N chimeras (Gearhart, J. D. et al., 1986, Brain Res. Bulletin 16:815-24) and by transplantation of fetal-derived Ts16 tissue into a 2N host (Holtzman, D. M. et al., 1992, Proc. Natl. Acad. Sci. 89:138387; Holtzman, D. M. et al., DOWN SYNDROME AND ALZHEIMER DISEASE, pp 227-44 (Wiley-Liss, New York, 1992).

Alzheimer's Disease and Amyloid Precursor Protein

Alzheimer's disease is a progressive dementia which is characterized by the precipitation of a peptide, termed an A β peptide, of about 40 amino acids within the brain and within the walls of blood vessels in the brain. The A β peptide is derived from the processing of a larger cell surface protein called the β Amyloid Precursor Protein (β APP). Production of the A β peptide is not per se pathological. The functions of both the A β peptide or β APP are unknown.

Several lines of evidence indicate that the deposition of the A β peptide is not merely correlative but rather causative of Alzheimer's disease. The gene encoding β APP is located on chromosome-21 and, as noted above, subjects having Down syndrome develop Alzheimer's disease. More directly, kinship groups have been identified among the many causes of familial Alzheimer's disease in which the inheritance of the Disease is linked to the inheritance of a gene encoding a mutated β APP, moreover the mutation is within the A β peptide itself. Reviewed Selkoe, D. J., 1994, Ann. Rev. Neurosci. 17:489-517. Transgenic mice, having multiple copies of such a mutant β APP gene, operatively linked to a strong, neuronal and glial cell specific promoter, develop the anatomical lesions of Alzheimer's disease at about 6-9 months of age. Games, D. et al., 1995, Nature 373:523.

There is a relationship between Down syndrome and Alzheimer's disease. The gene encoding the β APP is found on chromosome-21. Patients with Down syndrome are at increased risk of developing Alzheimer's disease or Alzheimer's-like pathology, most often by about the fifth decade of life although cases of earlier development have been reported. Mann, D. M. A. et al., 1990, Acta Neuropathol. 80:318-27.

Aids and Inceased IFN Levels

After a latency period that can last for many years, HIV infected individuals "convert" to the immunosuppressed state referred to as "AIDS". Acquired Immunodeficiency Syndrome ("AIDS") is a complex of various pathologies that is proceeded by and associated with increased levels of IFN-γ and IFN-α in the blood (Rossel, S. et al., 1989, J. Infectious Diseases 159:815-821) and IFN-α in the CSF (Rho, M B. et al., 1995, Brain, Behavior, and Immunity 9:366-77). Immunization with human IFN-α to reduce IFN levels is associated with the prevention of conversion to AIDS and improved prognosis for AIDS patients (Gringeri, A. et al., 1996, J AIDS and Human Retrovirology 13:55-67) as taught by Zagury, et al. (U.S. Pat. No. 6,093,405). However, this immunization procedure has serious limitations as it is both irreversible and unreliable.

Interferons, like cytokines in the body generally, do not act in the absence of antagonism (Van Weyenbergh, J. et al., 1998, J. Immunol. 161:1568-1574.; Paludan, S. R., 1998, Scand. J. Immunol. 48:459-468.; Ghosh, A. K. et al., 2001, J. Biol. Chem. 276:11041-11048) and/or synergy (Kwon, S. et al., 2001, Nitric Oxide 5:534-546.; Moore, P. E. et al., 2001, J. Appl. Physiol. 91:1467-1474.; Zhang, Y. et al., 2001, J. Interferon Cytokine Res. 21:843-850) caused by other cytokines or other interferon types. Note that some other cytokine combinations have been found to not be synergistic (Czuprynski, C. J. et al., 1992, Antimicrob. Agents Chemother. 36:68-70). In addition, the action of one type of interferon frequently can be mimicked or replaced by the action of another type of interferon (Hughes, T. K. et al., 1987, J Interferon Res. 7:603-614). There is speculation that if you inhibit IFN-γ and IFN-α then disease can be treated (Lachgar, A. et al., 1994, Biomed Pharmacother. 48:73-77, U.S. Pat. No. 5,780,027), however conflicting data in the literature suggests that combined treatment may, in some instances, not be more effective than monotherapy (Lukina, G. V. et al., 1998, Ter. Arkh. 70:32-37).

Presented herein is evidence demonstrating that the pathological negative effects of one type of interferon (IFN-γ) are in the body aided and enhanced in its negative effects by another type of interferon (IFN-α). These data demonstrate that the reduction of interferon bioactivity to relieve a pathological condition can be measurably improved by reducing the activity of both interferon types simultaneously. See, e.g., FIG. 3, which show the results of single vs. double knockout of interferon receptor genes.

SUMMARY OF THE INVENTION

The present invention is based, in part on the recognition that in certain pathologic processes, the host is rendered hyperproductive and/or aberrantly sensitive to the effects of interferon so that the effects of interferon become an immediate and direct cause of the pathology. Such processes include, in humans, trisomy of chromosome-21 or the portion of the chromosome-21 that encodes the receptor for type I interferon and at least one component of the receptor for IFN-γ, which is the genetic abnormality associated with Down syndrome. Other diseases where IFN plays an important role include Alzheimer's disease and late-stage HIV infection.

The present invention provides a method of ameliorating the pathologic effects of interferon by administering to a subject, in the above-noted circumstances, an antagonist of interferon. Embodiments of the invention include the administration of antagonists, alone or in combination, that are antagonists of Type I interferon, Type II interferon (IFN-γ), and placental interferon (IFN-τ).

The present invention relates to compositions of interferon antagonists that inhibit the activity of interferons from either animal and/or human sources such compositions being comprised of proteins, or dimers or fragments thereof, that bind to IFN-γ together with proteins, or dimers or fragments thereof, that bind to IFN-α such compositions thus binding to and inhibiting both IFN-γ and IFN-α. The present invention encompasses pharmacologically useful formulations of proteins that bind to and inhibit interferon comprising at least one IFN-γ binding protein plus at least one protein that binds to and inhibits one or more IFN-α subtypes that are appropriately modified as needed to provide for increased serum half-life, reduced immunogenicity, efficient mode of administration, increased binding affinity, and/or enhanced blood brain barrier (BBB) penetration.

The invention features a composition for preventing or decreasing the pathological effects of a disease, where the pathological effects are associated with an increased level of or a heightened responsiveness to interferon, where the composition comprises at least two isolated interferon binding proteins, and where the composition inhibits the activity of at least two different species of interferon. The species of interferon can comprise IFN-α and IFN-γ. The isolated interferon binding proteins can include a first interferon binding protein that binds to IFN-α and a second interferon binding protein that binds to IFN-γ. One or more of the interferon binding proteins can be an IFN-α binding protein. One or more of the interferon binding proteins can be an IFN-γ binding protein. One of the interferon binding proteins can be the human IFN-γ receptor. The interferon binding proteins can be the B8R and B18R proteins of Vaccinia virus. One of the interferon binding proteins can be Vaccinia B18R IFN-α binding protein. One of the interferon binding proteins can be the Vaccinia R8R interferon-γ binding protein. One or more of the interferon binding proteins can be an antibody, or an antibody fragment. One or more of the interferon binding proteins can be an interferon-specific antibody. One or more of the interferon binding proteins can be an interferon-specific humanized antibody. Antibodies or antibody fragments can be PEGylated or fused with transferrin. The interferon binding proteins can be PEGylated or fused with transferrin.

In another aspect, the invention features a plurality of interferon binding proteins comprising two or more interferon binding proteins, where the interferon binding proteins bind to and inhibit the activity of one or more interferons (i.e., interferon species).

Any of the compositions can be used in a method of treating a disease caused by elevated levels of two or more interferons, where the method includes the step of administering a therapeutically effective amount of the composition. The disease can be Alzheimer's disease, Down's syndrome, infant encephalitis, or an autoimmune disease. The disease can be HIV. Administration of the composition can be used to prevent the onset of AIDS.

In a further aspect, the invention features a method of treating a disease, where the method includes the step of administering a therapeutically effective amount of a pair of interferon antagonists to a patient having or at risk of having said disease, where the administration results in a reduction in the level of bioavailable interferon, such that the disease in the patient is treated. The disease can be Alzheimer's disease, Down's syndrome, infant encephalitis, or an autoimmune disease. The disease can be HIV. Administration of the composition can be used to prevent the onset of AIDS. Administration of the composition can be used to prevent or ameliorate AIDS-associated dementia. The interferon antagonists can be PEGylated or fused with transferrin.

In an additional aspect, the invention features a method of treating or preventing transplant rejection, where the method includes administering a therapeutically effective amount of one or more interferon antagonists to a patient, wherein the administration of the interferon antagonist reduces the level of bioavailable interferon in the patient such that the transplant rejection is treated or prevented. The interferon antagonists can be PEGylated or fused with transferrin.

The invention also features a method of treating or preventing AIDS in an HIV-infected patient, where the method includes administering a therapeutically effective amount of one or more interferon antagonists to the HIV infected patient, where the administration of the interferon antagonist reduces the level of bioavailable interferon in the patient such that AIDS in the HIV-infected patient is treated or prevented The interferon antagonists can be PEGylated or fused with transferrin. The one or more interferon antagonists can be a homodimer of the human IFN-γ receptor ligand binding subunits, or a heterodimer of the AR1 and AR2 ligand binding subunits of the human IFN-α receptor.

In an additional aspect, the invention features a method of treating or preventing IFN related disease using the B18R gene product or its homologs of viral or other origin. The B18R gene product or its homolog can be PEGylated, or fused to transferrin.

In a further aspect, the invention features a method of treating or preventing IFN related disease using the B8R gene product or its homologs of viral or other origin. The B18R gene product or its homolog can be PEGylated, or fused to transferrin.

The invention also features a composition for preventing or decreasing the pathological effects of a disease, wherein the pathological effects are associated with an increased level of or a heightened responsiveness to interferon, wherein said composition comprises one or more isolated interferon binding protein, and wherein the composition inhibits the activity of one or more species of interferon. The interferon binding protein can be PEGylated or fused with transferrin. The interferon binding protein can be PEGylated or fused with transferrin. The interferon binding protein can be B18R or B8R.

As used herein, "interferon binding proteins" refers to a protein or protein fragment or peptide that binds to interferons with a Kd binding constant of at least 10-3, preferably 10-5, more preferably 10-7 and most preferably 10-9 or less and inhibit the biological activity of the targeted interferon. The binding constants of typical interferon binding proteins are shown in Table 2, below.

As used herein, the term "interferons" refers to the different types of interferons (IFN), (Diaz, M. O. et al 1994, J Interferon Res. 14:221-222; Allen, D et al, 1996, J Interferon Res. 16:181-184). These five are designated a interferon (formerly α1), ω interferon (formerly ω2), β interferon, γ interferon, and τ interferon. The sequences of the α, β and γ interferons are shown in FIG. 7.

Interferon-α and -β are so-called type I interferons. They are secreted by a wide variety of cell types and have a wide range of functions. They are best known for their antiviral properties. They mediate their effects through the same receptor, which is present of the surfaces of virtually all nucleated cell types. Interferon-gamma (immune or type II interferon) is distinct in several ways from both interferon-alpha and -beta. It mediates its effects through a separate receptor from the one used by the type I interferons. In addition to having antiviral properties, it is especially noteworthy as a potent modulator of the functions of a wide range of cell types. Many of these functions are critical to the immune and inflammatory responses.

As used herein, INF-α refers to interferon-α subspecies and dimers thereof. INF-β refers to interferon-β subspecies and dimers thereof.

As used herein, to "inhibit the activity" refers to a decrease in the activity or available amount of an interferon that is at least 10%, preferably 10-30%, more preferably 30-50% and most preferably 50-100% decreased in the presence of one or more interferon binding proteins as compared to the activity of an interferon in the absence of the interferon binding proteins.

As used herein, the term "fusion polypeptide" or "fusion protein" refers to a polypeptide that is comprised of two or more amino acid sequences, wherein the two or more amino acid sequences are physically linked by a peptide bond and wherein the two or more amino acid sequences are not found linked in nature.

As used herein, an "iron transport protein" is a transferrin preferably selected from the group comprising human transferrin, lactoferrin, ovotransferrin and/or serum transferrin.

As used herein, "Vaccinia B18R IFN-α binding protein" refers to a glycoprotein (60-65 kDa; see FIG. 8 that exists in a soluble and a membrane-bound form. The protein functions as a type-1 interferon (IFN) receptor with broad species specificity. The B18R protein has high affinity for human IFN-α and also binds rabbit, bovine, rat, pig, and mouse IFN-α. Since the protein exists as a soluble extracellular and a cell surface protein it has the potential to block both autocrine and paracrine functions of IFN. The B18R protein has been shown to inhibit the antiviral potency of IFN-α-1, IFN-α-2, IFN-α-8/1/8, and IFN-Ω on human cells.

As used herein, "Vaccinia B8R interferon γ binding protein" refers to a protein encoded by the B8R open reading frame of vaccinia virus (see FIG. 8). B8R possesses a hydrophobic amino-terminal signal sequence but lacks a discernible membrane anchor domain, suggesting that the proteins may be secreted.

As used herein, "modified to enhance drug delivery" refers to modifications of interferon antagonists so as to fiacilitate their delivery to a target tissue. In one embodiment the invention includes post-translational modification of interferon antagonists (for example PEGylation or glycation). In a further embodiment the interferon antagonist is fused to a fusion protein. In a preferred embodiment the fusion protein is an iron transport protein that promotes transport of the interferon antagonist across the blood brain barrier. In a further embodiment, the interferon antagonist is fused to a fusion protein that is capable of multimerization.

As used herein, a "therapeutically effective amount" means the total amount of each active component of the pharmaceutical composition or method that is sufficient to show a meaningful patient benefit, i.e., in the treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously. Generally, a composition will be administered in a single dose in the range of 100 μg-10 mg/kg body weight, preferably in the range of 1 μg-100 μg/kg body weight. This dosage may be repeated daily, weekly, monthly, yearly, or as considered appropriate by the treating physician.

As used herein, "interferon antagonist" refers to a biomolecule that binds to an interferon as defined herein and blocks the biological activity of the interferon. In a preferred embodiment the interferon antagonist of the invention is an interferon binding protein. The effective amount of an interferon antagonist needed to bind and block interferon proteins in the blood can be determined by assaying the concentration of bioavailable interferon. An effective dose of interferon antagonist is a dose that is sufficient to reduce the level of bioavailable interferon by between at least three to five fold, more preferably by about ten fold and most preferably by about twenty five fold below the normal levels of interferon. The interferon antagonist can be a mixture of antagonists that are specific for the various different types of interferon. When one type of interferon predominates, the antagonist can be an antagonist for only the predominate type of interferon that is present.

As used herein, "transplant rejection" refers to the immune response that results from the transfer of a donor's cells, tissues or organs into a histoincompatible host.

As used herein, "treating a disease" refers to arresting or otherwise ameliorating the symptoms of a disease at least 10%, preferably 20-50% and more preferably 75-100%.

As used herein, the term "autoimmune disease" refers to a disorder wherein the immune system of a mammal mounts a humoral or cellular immune response to the mammal's own tissue or has intrinsic abnormalities in its tissues preventing proper cell survival without inflammation, Examples of autoimmune diseases include, but are not limited to, diabetes, rheumatoid arthritis, multiple sclerosis, lupus erythematosis, myasthenia gravis, scieroderma, Crohn's disease, ulcerative colitis, Hashimoto's disease, Graves' disease, Sjögren's syndrome. polyendocrine failure, vitiligo, peripheral neuropathy, graft-versus-host disease, autoimmnune polyglandular syndrome type L, acute glomerulonephritis, Addison's disease, adult-onset idiopathic hypoparathyroidism (AOIH), alopecia totalis, amyotrophic lateral sclerosis, ankylosing spondylitis, autoimmune aplastic anemia, autoimmune hemolytic anemia, Behcet's disease, Celiac disease, chronic active hepatitis, CREST syndrome, dermatomyositis, dilated cardiomyopathy, eosinophilia-myalgia syndrome, epidermolisis bullosa acquisita (EBA), giant cell arteritis, Goodpasture's syndrome, Guillain-Barré syndrome, hemochromatosis, Henoch-Schönlein purpura, idiopathic IgA nephropathy, insulin-dependent diabetes mellitus (IDDM), juvenile rheumatoid arthritis, Lambert-Eaton syndrome, linear IgA dermatosis, myocarditis, narcolepsy, necrotizing vasculitis, neonatal lupus syndrome (NLE), nephrotic syndrome, pemphigoid, pemphigus, polymyositis, primary sclerosing cholangitis, psoriasis, rapidly-progressive glomerulonephritis (RPGN), Reiter's syndrome, stiff-man syndrome and thyroiditis.

As used herein, "infant encephalitis" refers to inflammation of the brain most commonly caused by a viral infection of the brain that occurs in young children. The most important viruses causing sporadic cases of encephalitis in immunocompetent adults are herpes simplex virus type 1 (HSV-1), varicella-zoster virus (VZV), and, less commonly, enteroviruses. Epidemics of encephalitis are caused by arboviruses, which belong to several different viral taxonomic groups including Alphavirus of the family Togaviridae (e.g., Eastern equine encephalitis virus, Western equine encephalitis virus), Flavivirus of the family Flaviviridae (e.g., St. Louis encephalitis virus, Powassan virus), and Bunyavirus of the family Bunvaviridae (e.g., California encephalitis virus serogroup, LaCrosse virus).

As used herein, "bioavailable" refers to the portion of interferon that can be absorbed, transported, and/or utilized physiologically.

As used herein, the term "immunoglobulin" or "antibody" refers to a conventional antibody molecule, as well as fragments thereof which are also specifically reactive with one of the subject polypeptides. Antibodies can be fragmented using conventional techniques, e.g., protein digestion, gene truncation, and the fragments screened for utility in the same manner as described herein for whole antibodies. For example, F(ab)2 fragments can be generated by treating antibody with pepsin. The resulting F(ab)2 fragment can be treated to reduce disulfide bridges to produce Fab fragments. The antibodies and antibody fragments can be screened for enhanced binding affinity using phage display technology. The antibody of the present invention is further intended to include bispecific, single-chain, and chimeric and humanized molecules having affinity for a polypeptide conferred by at least one CDR region of the antibody. In preferred embodiments, the antibody further comprises a label attached thereto and able to be detected, (e.g., the label can be a radioisotope, fluorescent compound, chemiluminescent compound, enzyme, or enzyme co-factor). The antibodies, monoclonal or polyclonal and its hypervariable portion thereof (FAB, FAB2, etc.) as well as the hybridoma cell producing the antibodies are a further aspect of the present invention which find a specific industrial application in the field of diagnostics and monitoring of specific diseases, preferably the ones hereafter described. In a preferred embodiment, the immunoglobulin is humanized.

"Humanized antibody", as used herein, refers to antibody molecules in which amino acids have been replaced in the non-antigen binding regions in order to more closely resemble a human antibody, while still retaining the original binding ability. Methods for making humanized antibodies are described in U.S. Pat. Nos. 6,054,297, 5,859,205, which are hereby incorporated be reference in their entirety.

As used herein, "in frame" refers to the reading frame used for the translation of a fusion polypeptide nucleotide sequence. In a fusion polypeptide X-Y, coding sequences for polypeptide Y are said to be 'in frame' with upstream coding sequences for the polypeptide X if the translation of the coding sequences X-Y results in a fusion polypeptide wherein polypeptide X is fused to polypeptide Y.

As used herein, the "pathological effects are associated with an increased level of, or a heightened responsiveness to, interferon" refers to a disease state that is associated with elevated levels of IFN receptors on the patient's cells or bioavailable interferon in the bodily fluids of a patient afflicted with the disease. For example, FIG. 3 shows evidence that the pathological negative effects of one type of interferon (IFN-γ) in this instance, growth retardation of a trisomy 16 mouse fetus is enhanced in its negative effects by another type of interferon (IFN-α). These data on growth retardation also demonstrate that reduction of interferon bioactivity through gene knock out mutations in the IFN-γ and/or IFN-α/β receptors results in reduction in the pathological condition i.e., growth retardation and that this reduction is enhanced if the activity of both interferon types, i.e., IFN-γ and IFN-α are reduced simultaneously.

As used herein, the term "Human Immunodeficiency Virus" or "HIV" is meant to refer to all strains of human immunodeficiency viruses. Active human immunodeficiency virus infection results in a decline in the number of CD4+ T cells, which in turn results in the incapacity of the infected individual to mount an effective immune response to viral, bacterial, fungal or parasitic infections.

As used herein, the "AIDS" refers to HIV infected patients with a CD4+ T cell count of less than <200/μL and who develop one of the HIV-associated diseases considered to be indicative of a severe defect in cell-mediated immunity, typically opportunistic infections by organisms such as *P. carinii*, atypical mycobacteria, CMV, fungi, and other organisms that do not ordinarily cause disease in the absence of a compromised immune system.

As used herein, AIDS in an HIV infected patient is said to he "treated" or "prevented" if the CD4+ T cell count remain at or increases to a value that is 25%, 50%, 75%, 90%, 99% or preferably equal to the CD4+ T cell count of a patient that is not infected with HIV.

As used herein, the onset of AIDS in an HIV infected patient is said to be "prevented" if the patient's CD4+ T cell count decreases no more than 25%, preferably 10%, most preferably 0% from the CD4+ T cell count of a patient who is not infected with HIV.

DESCRIPTION OF THE FIGURES

FIG. 1A, Uninjected controls; FIG. 1B, non-specific IgG (ns-IgG) injected controls; FIG. 1C, anti-IFN injected fetuses. An analysis-of-covariance was performed to compare the groups on length while adjusting for average normal littermate length. The lengths of the anti-IFN treated group were significantly greater than those of the ns-IgG injected controls ($p=0.0112$) and those of the uninjected controls ($p=0.0037$). The dotted lines in each figure encompass the 95% confidence limits.

FIG. 2A, average eye opening of 17 to 23 mm trisomy 16 fetuses; FIG. 2B, average back curvature scores of trisomy 16 fetuses greater than 20 mm in length. Columns. (A) Uninjected; (B) non-specific IgG injected; (C) anti-IFN injected; (D) euploid. The mean. +/−standard error is presented.

FIG. 4A: PCR amplification of the B18R Vaccinia gene (agarose gel electrophoresis). Lane 1: Lambda DNA HindIII digest markers; Lane 2: B18R gene PCR product (expected length, 999 bp). FIG. 4B: Restriction enzyme digests of the mammalian expression plasmid carrying the B18R Vaccinia gene (agarose gel electrophoresis). Lane 1: HindIII digest of the plasmid (there are no HindIII sites in the insert and there is one HindIII site in the original plasmid); Lane 2: BglII plasmid digest (there is one BglII site in the insert and one BglII site in the original plasmid); and Lane 3: Lambda DNA HindIII digest markers.

FIGS. 7A, 7B, 7C: Genbank Accession numbers of the interferons (SEQ ID NOS 9-18 respectively, in order of appearance).

FIGS. 8A and 8B: Nucleotide and amino acid sequence of B18R and B8R gene products of Vaccinia virus (B8R, Genbank Accession No.: AFO162273; B18R (FIG. 8A), GenBank Accession No.: D90076 (FIG. 8B)) (SEQ ID NOS 19-22 respectively, in order of appearance).

DETAILED DESCRIPTION OF THE INVENTION

Figure 1A:
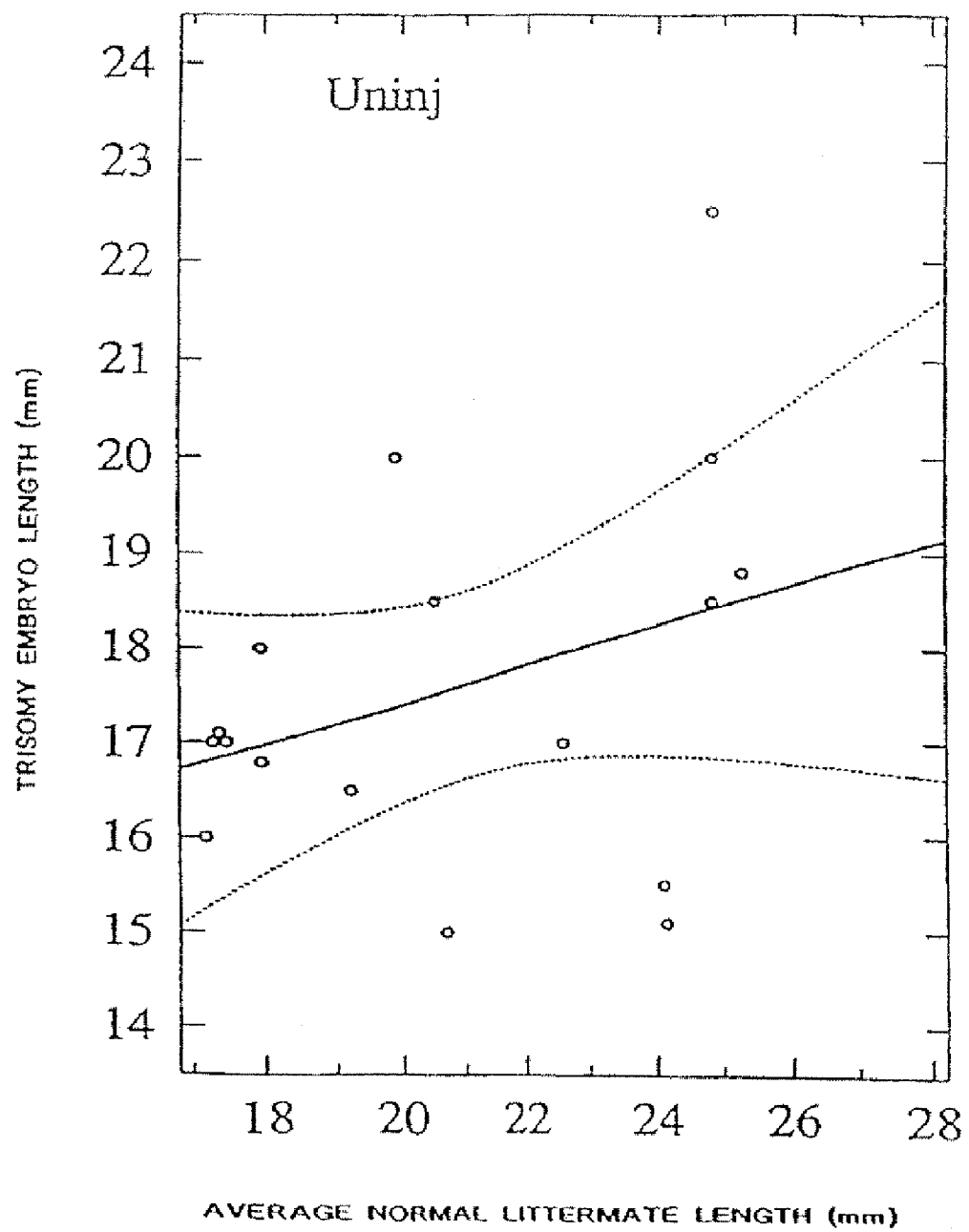
FIGS. 1A-1C. The lengths of Trisomy 16 fetuses plotted as a function of the average length of normal littermates.

The present invention provides a method of ameliorating the pathologic effects of interferon by administering to a subject, in the above-noted circumstances, an antagonist of interferon. Embodiments of the invention include the administration of antagonists, alone or in combination, that are antagonists of Type I interferon, Type II interferon (IFN-γ), and placental interferon (IFN-τ).

Many different species of virus produce interferon-binding proteins as a means of reducing the ability of the host to mount an immune response to infection, Examples of interferon binding proteins of the invention are depicted in Table 1, below, and share the property of being able to bind IFN-α or IFN-γ with high affinity, as shown in Table 2.

TABLE 2

Examples of binding constants of interferon binding proteins.

| | Kd | Reference |
|---|---|---|
| Gamma-IFN: | | |
| Myxoma M-T7 | $1.2 \times 10^{-9}$ M | Bai, H. et al., 2002, Biotechniques 32: 160, 162-4, 166-71. |
| Vaccinia B8R | Undetermined | |
| Human gamma receptor | $1\text{-}2 \times 10^{-9}$ M | Fountoulakis, M. et al., 1990, J. Biol. Chem. 265: 13268-75 |

TABLE 2-continued

Examples of binding constants of interferon binding proteins.

| | Kd | Reference |
|---|---|---|
| Alpha-IFN: | | |
| Vaccinia B18R | $174 \times 10^{-12}$ M | Symons, J. A. et al., 1995, Cell 81: 551-60 |
| Human alpha receptor | $1 \times 10^{-7}$ M (in solution) $1 \times 10^{-9}$ M (cell surface) | Nguyen, N. Y. et al., 1996, J Interferon Cytokine Res 16 835-44 |
| Immunoglobin (Ig) | $10^{-11}$ M $10^{-7}$ (Ag) to $10^{-8}$ M (peptide) | Darsley, M. J. et al., 1985, Embo J. 4: 383-92; Klein, B. et al., 1995, Immunol Today 16: 216-20 |

In order to ensure a successful infection, viruses use many different strategies to suppress or circumvent the host immune response. For example, the CrmA gene encoded by poxvirus functions by inhibiting interleukin-1 beta converting enzyme (Pickup, D. J., Infect. Agents Dis. 3(2-3):116-127 (1994), the SERP-1 gene of Myxoma virus encodes a serine protease inhibitor (McFadden, G. et al., J. Leukoc. Biol. 57(5):731-738 (1995)) and, the Myxoma virus encodes a TNF receptor homologue (T2, U.S. Pat. No. 5,464,938).

"Cytokine binding proteins" belong to a group of virally coded proteins termed "viroceptors" (Upton et al., Virology, 184:370 (1991)) as they act as decoy receptors to bind to cytokines thereby diverting the cytokine away from its normal host cell surface receptor. The term "virally encoded interferon binding proteins" refers to a viroceptor that binds to and inhibits one or more interferon types.

The Myxoma virus also encodes an IFN binding protein M-T7 that is described in U.S. Pat. No. 5,834,319. However, the M-T7 protein is of limited utility as it does not bind to interferon of human origin (see, e.g., U.S. Pat. No. 5,834,419). In contrast, the B8R and B18R proteins encoded by the poxviruses which are the subject of the present invention (FIG. 8) bind to and strongly inhibit the activity of human IFN-γ (B8R) and human IFN-α (B18R).

In some instances it may be preferable to use an IFN binding protein of human origin. The present invention describes highly modified forms of the human IFN-γ and IFN-α/β receptors that provide for increased binding affinity, serum half-life, and enhanced blood-brain-barrier (BBB) penetration.

Selection of Subjects

The present invention concerns the administration of interferon antagonists to subjects in order to ameliorate the neurological, pathological, and developmental abnormalities in the subject due to the action of interferon. A particular group of subjects at risk are subjects having a trisomy of the portion of the chromosome region, designated in humans 21q21.1-21.31, that encodes for interferon receptors. This group has the clinical diagnosis of Down syndrome. Grete, N., 1993, Eur. J. Hum, Genetics 1:51-63; Sinet, P. M., 1994, Biomed. & Pharmacol. 48:247-252. The homologous chromosome in mice is chromosome-16.

Diagnosis of Down syndrome can be made by any method known to the medical arts. Typically, for diagnosis in utero, amniocentesis can be performed at about 14 weeks of gestational age and chorionic villus sampling (biopsy) can be performed between 9 and 12 weeks of gestational age. Down syndrome in children and adults is diagnosed from karyotypes of peripheral blood cells. Cells from either type of sample are cultured and cytogenetic examination can be performed by methods well understood by those skilled in the art.

As noted above, patients having Down syndrome are at increased risk to develop Alzheimer's disease. A further group of subjects that would benefit from the invention consist of subjects having the diagnosis of probable Alzheimer's disease or who are at increased risk of developing Alzheimer's disease from causes other than Down syndrome. The diagnosis of probable Alzheimer's disease is made by clinical criteria (McKhann, G., 1984, Neurology 34:939; DIAGNOSTIC AND STATISTICAL MANUAL OF MENTAL DISORDERS IV, American Psychological Association, Washington, D.C.). Persons having a familial predisposition to Alzheimer's disease are also suitable subjects for the present invention.

HIV Infected Pre-AIDS and AIDS Patients

A further group of patients that would benefit from this invention consist of subjects having the diagnosis of HIV infection who have developed, or are at risk of developing, the AIDS complex of pathologies associated with immunosuppression. In these individuals, the conversion to the AIDS complex is proceeded by, and associated with, increased IFN-γ and IFN-α bioactivity which can be determined by various methods well known to the medical arts.

The Selection of Antagonists

The antagonist of the invention can be any antagonist that can be administered to the subject in an amount effective to prevent the deleterious action of the interferon.

The effective amount of antagonists that act by binding to and blocking interferon proteins in the blood can be determined by assaying the concentration of bioavailable interferon in the subjects blood. An effective dose of antagonist is a dose that is sufficient to reduce the level of bioavailable interferon by between at least three to five fold, more preferably by about ten fold and most preferably by about twenty five fold below the normal levels of interferon.

The assay of bioavailable interferon is performed by adding a sample of the subjects blood to a culture of an interferon sensitive cell line which is then infected with a test virus, typically Vesicular Stomatitis Virus (VSV), and the number of viral plaques is determined or the cytotoxic effects of the VSV infection is otherwise quantitated. Bioavailable interferon blocks productive viral infection. The level of bioavailable interferon is calculated by comparing various dilutions of the test sample with a titration of a standard sample of interferon. Such assays are routine in the art. See, e.g., Hahn, T. et al., 1980, in INTERFERON: PROPERTIES AND CLINICAL USES, ed. by A. Khan, N. O. Hill and G. L. Dorn, (Leland Fikes Foundation Press, Dallas, Tex.); Armstrong, J. A., 1971, Applied Microbiology 21:723-725; Havell, E. A. & Vilcek, J. 1972, Anti-microbial Agents and Chemotherapy 2:476-484.

In one embodiment of the invention the antagonist is a monoclonal anti-interferon antibody or fragment thereof. The production of such antibodies is well known in the art. The production of anti-IFN-α monoclonal antibodies that block interferon activity is taught by U.S. Pat. No. 4,973,556 to Bove et al. The production of blocking monoclonal antibodies to IFN-γ is taught by U.S. Pat. No. 4,948,738 to Banchereau. The structure of human trophoblastic interferon (IFN-τ) has been recently disclosed (Whaley, A. E., 1994, J. Biol. Chem. 269:10864-8). Monoclonal antibodies and other antagonists to this interferon can be produced using methods well know to those skilled in the art.

In a preferred embodiment, the antibody is a "chimeric" antibody, i.e., an antibody having a variable region from one species and a constant region from another species. Most typically chimeric antibodies for use in humans have constant regions of human origin. In an alternative preferred embodiment, the antibody is a "grafted" antibody, i.e., an antibody having complementarity determining regions from one species and a constant region and a framework region of the variable region from a second species. A grafted antibody in which the second species is human is termed a "humanized" antibody. Methods of making chimeric antibodies suitable for pharmaceutical use are disclosed in International Patent publication WO 92/16553 by Le, J. (Oct. 1, 1992). "Grafted" antibodies and "humanized" antibodies are described in U.S. Pat. No. 5,225,539 to Winter and International Patent publications WO 91/09967 and WO 92/11383 by Adair, J. R. et al. Suitable antagonists, smaller than an antibody molecule, can be derived from anti-interferon monoclonal antibodies by techniques well known in the art. See, e.g. U.S. Pat. No. 5,091,513 to Huston and U.S. Pat. No. 5,260,203 to Ladner. As used herein the term "antibody antagonists" includes natural polyclonal and monoclonal antibodies, chimeric and grafted antibodies, and antibodies produced by human antibody gene trangenic animals, and enzymatically and recombinantly produced interferon binding fragments of each type of antibody.

In an alternative embodiment the antagonist can be a recombinantly produced protein that comprises the interferon binding portion of an interferon receptor. The production of soluble interferon receptors by baculovirus transduced cells is described in Fountoulakis et at., 1991, Eur. J. Biochem. 198:441-450. Alternatively the antagonist can be a fusion protein that contains an interferon binding domain of an interferon receptor.

In alternative embodiments, the antagonist can be an antibody to an interferon receptor, a soluble interferon receptor, receptor fragment, or a peptide that is derived from an interferon that occupies the receptor binding site but does not activate the receptor. Such an IFN-γ peptide antagonist is disclosed by Jarpe, M. A. et al., 1993, J. Interferon Res. 13:99-103.

When the subject is a fetus, or an infant less than 6 weeks of age, the blood brain barrier is not fully formed. In these circumstances antibodies and other proteins that block the interferon receptor can directly reach the central nervous system. When the subject has an intact blood brain barrier, an embodiment of the invention can employ antibodies and proteins that block interferon by binding the interferon directly, rather than those that act at the interferon receptor.

Alternatively, increased CNS entry of antibody antagonists can be obtained by chemical modification of the antagonist. Such modifications include cationization, Pardridge, W., 1991, "Peptide Drug Delivery to the Brain", and glycation, Poduslo, J. F. & Curran, G. L., 1994, Molecular Brain Research 23:157.

The interferon antagonist can be a mixture of antagonists that are specific for the various different types of interferon. When one type of interferon predominates, the antagonist can be an antagonist for only the predominate type of interferon that is present.

When the subject is a fetus, then the antagonist can be administered by a transplacental route, e.g., antibody that is transported across the placenta. The human isotypes IgG1, IgG3 and IgG4 are suitable for transplacental administration.

Interferon Antagonists

In a preferred embodiment, Interferon binding proteins particularly useful for the formulation of the type of interferon antagonist described in the present invention are the B18R and B8R gene products of Vaccinia virus (B8R; B18R, see FIG. 8). The B8R protein is an IFN-γ binding protein that will bind and inhibit IFN-γ from human, rat, or rabbit sources (Alcami, A. et al., 1995, J. Virol. 69:4633-4639). The cross-species binding ability of these proteins greatly improves their utility as their ability to bind interferon, and the side effects of this binding, can be tested in animals prior to the start of human trials. In addition, the B18R protein is an IFN-α binding protein that is a single polypeptide that will bind and inhibit numerous subspecies of IFN-α from various sources (e.g., human, rat, mouse, or rabbit) (Symons, J. A. et al., 1995, Cell. 81:551-560).

In another embodiment, the invention is comprised of proteins of both viral and human origin. For example, the human IFN-γ receptor, or dimer or fragment or modification thereof, could be in a composition with the Vaccinia B18R protein, or dimer or fragment or modification thereof. The isolation and preparation of IFN-γ receptors is taught by U.S. Pat. Nos. 5,578,707, 5,221,789, and 5,763,210. The human IFN-γ ligand-binding gene can be cloned and expressed using standard procedures. For example, this gene can be PCR amplified from a thymus cDNA library (Clontech, Palo Alto, Calif., USA) using the procedures and primers described herein (see FIG. 5).

The genes encoding the IFN binding proteins of the invention can be isolated and expressed in prokaryotic or eukaryotic systems using methods familiar to those practiced in the art of gene cloning and expression.

Interferon Antagonist Fusion Proteins

The invention provides for interferon antagonist fusion proteins, fragments, dimiers and modifications thereof. Methods used to link the cDNA nucleic acid encoding a gene of interest, or portion thereof, in frame, to a nucleic acid encoding interferon antagonist are well known to those in the art and are described extensively in Ausubel et al., eds., Current Protocols in Molecular Biology, John Wiley & Sons, Inc., 1995, with supplemental updates. The encoded-protein of interest may be linked in-frame to the amino-or carboxyl-terminus of the interferon antagonist. The nucleic acid encoding the chimeric protein is then linked in operable association to a promoter element of a suitable expression vector. Fusion partners are chosen to confer specific properties to the interferon antagonist such as the ability to dimerize or multimerize or the ability to traverse the blood-brain barrier.

In a preferred embodiment of the invention, interferon antagonists are fused to the human transferrin protein, e.g., Genbank accession number: XM_002793 which facilitates passage across the blood brain barrier (see "Modifications of Interferon Antagonist Proteins", infra).

In a preferred embodiment of the invention, interferon antagonists are dimers with an enhanced binding affinity for interferons. For example, human IFN-γ can be a dimer, and its interaction with the homodimer of IFN-γ ligand-binding subunits provides a significantly stronger bond than one subunit alone. This improvement in binding affinity has been demonstrated by Moosmayer and co-workers (Moosmayer, D. et al., 1995, J. Interferon. Cytokine Res. 15:1111-1115). An example of the human IFN-γ receptor fragment modified to form a dimer and further modified to enhance BBB transport via fusion to the human transferrin protein is presented in FIG. 6A.

Primers According to the Invention

The invention provides for oligonucleotide primers useful for amplifying interferon antagonist sequences, such as those cDNA sequences that encode the Vaccinia B8R or B18R proteins.

Primer Design

Primers may be selected manually by analyzing the template sequence. Computer programs, however, are also available in selecting primers to generate an amplified product with a designed length, e.g., primer premier 5 and primer 3.

It is known in the art that primers that are about 20-25 bases long and with 50% G-C content will work well at annealing temperature at about 52-58° C. These properties are preferred when designing primers for the subject invention. Longer primers, or primers with higher G-C contents, have annealing optimums at higher temperatures; similarly, shorter primers, or primers with lower G-C contents, have optimal annealing properties at lower temperatures, A convenient, simplified formula for obtaining a rough estimate of the melting temperature of a primer 17-25 bases long is as follows:

$$\text{Melting temperature (Tm in } ^\circ\text{ C.)}=4\times(\text{\# of } G+\text{\# of } C)+2\times(\text{\# of } A+\text{\# of } T)$$

Shorter fragments are amplified more efficiently than longer fragments although target of more than 10 kb can be successfully amplified. Therefore preferably primers are selected so to amplify a relatively short product. Preferably, primers are selected to generate an amplified product of less than 500 bp, or 200 bp, or more preferably 100 bp in length or most preferably 73 bp in length.

In accordance with the preferred embodiments, optimal results have been obtained using primers, which are 19-25 in length. However, one skilled in the art will recognize that the length of the primers used may vary. For example, it is envisioned that shorter primers containing at least 15, and preferably at least 17, may be suitable. The exact upper limit of the length of the primers is not critical. However, typically the primers will be less than or equal to approximately 50 bases, preferably less than or equal to 30 bases.

Primer Synthesis

Methods for synthesizing primers are available in the art. The oligonucleotide primers of this invention may be prepared using any conventional DNA synthesis method, such as, phosphotriester methods such as described by Narang et al. (1979, Meth. Enzymol., 68:90) or Itakura (U.S. Pat. No. 4,356,270), or and phosphodiester methods such as described by Brown et al. (1979, Meth. Enzymol., 68:109), or automated embodiments thereof, as described by Mullis et al. (U.S. Pat. No. 4,683,202). Also see particularly Sambrook et al. (1989), Molecular Cloning: A Laboratory Manual (2d ed.; Cold Spring Harbor Laboratory, Plainview, N.Y.), herein incorporated by reference.

Vectors Useful According to the Invention

There is a wide array of vectors known and available in the art that are useful for the expression of interferon antagonists according to the invention. The selection of a particular vector clearly depends upon the intended use. For example, the selected vector must be capable of driving expression of the interferon antagonist or variant thereof in the desired cell type, whether that cell type be prokaryotic or eukaryotic. Many vectors comprise sequences allowing both prokaryotic vector replication and eukaryotic expression of operably linked gene sequences.

Vectors useful according to the invention may be autonomously replicating, that is, the vector, for example, a plasmid, exists extrachromosomally and its replication is not necessarily directly linked to the replication of the host cell's genome. Alternatively, the replication of the vector may be linked to the replication of the host's chromosomal DNA, for example, the vector may be integrated into the chromosome of the host cell as achieved by retroviral vectors and in stably transfected cell lines. Vectors useful according to the invention preferably comprise sequences operably linked to an interferon antagonist protein coding sequences that permit the transcription and translation of fusion protein polynucleotide sequences. The term "transcriptional regulatory sequences" refers to the combination of a promoter and any additional sequences conferring desired expression characteristics (e.g., high level expression, inducible expression, tissue-or cell-type-specific expression) on an operably linked nucleic acid sequence. An "expression vector", according to the invention, comprises either an inducible promoter, or a tissue-specific promoter. A constitutive promoter such as viral promoters or promoters from mammalian genes., are generally active in promoting transcription. Examples of constitutive viral promoters include the HSV, TK, RSV, SV40 and CMV promoters, of which the CMV promoter is a currently preferred example. Examples of constitutive mammalian promoters include various housekeeping gene promoters, as exemplified by the β-actin promoter. Inducible promoters and/or regulatory elements are also contemplated for use with the expression vectors of the invention. Examples of suitable inducible promoters include promoters from genes such as cytochrome P450 genes, heat shock protein genes, metallothionein genes, hormone-inducible genes, such as the estrogen gene promoter, and the like. Promoters that are activated in response to exposure to ionizing radiation, such as fos, jun and egr-1, are also contemplated. The tetVP16 promoter that is responsive to tetracycline is a currently preferred example. Tissue-specific promoters are also contemplated for use with the expression vectors of the invention. Examples of such promoters that may be used with the expression vectors of the invention include promoters from the liver fatty acid binding (FAB) protein gene, specific for colon epithelial cells; the insulin gene, specific for pancreatic cells; the transphyretin, α 1-antitrypsin, plasminogen activator inhibitor type 1 (PAI-1), apolipoprotein AI and LDL receptor genes, specific for liver cells; the myelin basic protein (MBP) gene, specific for oligodendrocytes; the glial fibrillary acidic protein (GFAP) gene, specific for glial cells; OPSIN, specific for targeting to the eye; and the neural-specific enolase (NSE) promoter that is specific for nerve cells.

The selected promoter may be any DNA sequence that exhibits transcriptional activity in the selected host cell, and may be derived from a gene normally expressed in the host cell or from a gene normally expressed in other cells or organisms. Examples of promoters include, but are not limited to the following: prokaryotic promoters: *E. coli* lac, tac, or trp promoters, lambda phage PR or PL promoters, bacteriophage T7, T3, Sp6 promoters, *B. subtilis* alkaline protease promoter, and the *B. stearothermophilus* maltogenic amylase promoter, etc.; eukaryotic promoters: yeast promoters, such as GAL1, GAL4 and other glycolytic gene promoters (see for example, Hitzeman et al., 1980, J. Biol. Chem. 255: 2073-12080; Alber & Kawasaki, 1982, J. Mol. Appl. Gen. 1:419-434), LEU2 promoter (Martinez-Garcia et al., 1989, Mol. Gen. Genet. 217:464-470), alcohol dehydrogenase gene promoters (Young et al., 1982, in Genetic Engineering of Microorganisms for Chemicals. Hollaender et al., eds., Plenum Press, NY), or the TPI1 promoter (U.S. Pat. No. 4,599,311); insect promoters, such as the polyhedrin promoter (U.S, Pat. No. 4,745,051 Vasuvedan et al., 1992, FEBS Lett. 311:7-11), the P10 promoter (Vlak et al., 1988, J. Gen. Virol. 69:765-776), the *Autographa californica* polyhedrosis virus basic protein promoter (EP 397485), the baculovirus immediate-early gene 1 promoter (U.S. Pat. Nos. 5,155,037 and 5,162,222), the baculovirus 39K delayed-early gene promoter (also U.S. Pat. Nos. 5,155,037 and 5,162,222) and the OpMNPV immediate early promoter 2; mammalian promoters: the SV40 promoter (Subramani et al., 1981, Mol. Cell. Biol. 1:854-864), metallothionein promoter (MT-1; Palmiter et al., 1983, Science 222: 809-814), adenovirus 2 major late promoter (Yu et al., 1984, Nucl. Acids Res, 12:9309-21), cytomegalovirus (CMV) or other viral promoter (Tong et al., 1998, Anticancer Res. 18:719-725), or even the endogenous promoter of a gene of interest in a particular cell type.

A selected promoter may also be linked to sequences rendering it inducible or tissue-specific, For example, the addition of a tissue-specific enhancer element upstream of a selected promoter may render the promoter more active in a given tissue or cell type. Alternatively, or in addition, inducible expression may be achieved by linking the promoter to any of a number of sequence elements permitting induction by, for example, thermal changes (temperature sensitive), chemical treatment (for example, metal ion-or IPTG-inducible), or the addition of an antibiotic inducing agent (for example, tetracycline).

Regulatable expression is achieved using, for example, expression systems that are drug inducible (e.g., tetracycline, rapamycin or hormone-inducible). Drug-regulatable promoters that are particularly well suited for use in mammalian cells include the tetracycline regulatable promoters, and glucocorticoid steroid-, sex hormone steroid-, ecdysone-, lipopolysaccharide (LPS)-and isopropylthiogalactoside (IPTG)-regulatable promoters. A regulatable expression system for use in mammalian cells should ideally, but not necessarily, involve a transcriptional regulator that hinds (or fails to bind) non mammalian DNA motifs in response to a regulatory agent, and a regulatory sequence that is responsive only to this transcriptional regulator.

There are a number of well known bacteriophage-derived vectors useful according to the invention. Foremost among these are the lambda-based vectors, such as Lambda Zap II or Lambda-Zap Express vectors (Stratagene) that allow inducible expression of the polypeptide encoded by the insert. Others include filamentous bacteriophage such as the M13-based family of vectors.

A number of different viral vectors are useful according to the invention, and any viral vector that permits the introduction and expression of sequences encoding interferon antagonist polypeptides or variants thereof in cells is acceptable for use in the methods of the invention. Viral vectors that can be used to deliver foreign nucleic acid into cells include but are not limited to retroviral vectors, adenoviral vectors, adeno-associated viral vectors, herpesviral vectors, and Semiliki forest viral (alphaviral) vectors and Vaccinia viruses. Defective retroviruses are well characterized for use in gene transfer (for a review see Miller, A. D. (1990) Blood 76:271). Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14, and other standard laboratory manuals.

In addition to retroviral vectors, Adenovirus can be manipulated such that it encodes and expresses a gene product of interest but is inactivated in terms of its ability to replicate in a normal lytic viral life cycle (see for example Berkner et ala, 1988, BioTechniques 6:616; Rosenfeld et al., 1991, Science 252:431-434; and Rosenfeldet al., 1992, Cell 68:143-155). Suitable adenoviral vectors derived from the adenovirus strain Ad type 5 d1324 or other strains of adenovirus (e.g., Ad2, Ad3, Ad7 etc.) are well known to those skilled in the art. Adeno-associated virus (AAV) is a naturally occurring defective virus that requires another virus, such as an adenovirus or a herpes virus, as a helper virus for efficient replication and a productive life cycle. For a review see Muzyczka et al., 1992, Curr. Topics in Micro. and Immunol. 158:97-129, An AAV vector such as that described in Traschin et al. (1985, Mol. Cell. Biol. 5:31 251-3260) can be used to introduce nucleic acid into cells. A variety of nucleic acids have been introduced into different cell types using AAV vectors (see, for example, Hermonat et al., 1984, Proc. Natl. Acad. Sci. USA 81:6466-6470; and Traschin et al., 1985, Mol. Cell. Biol. 4:2072-2081).

The introduction and expression of foreign genes is often desired in insect cells because high level expression may be obtained, the culture conditions are simple relative to mammalian cell culture, and the post-translational modifications made by insect cells closely resemble those made by mammalian cells. For the introduction of foreign DNA to insect cells, such as *Drosophila* S2 cells, infection with baculovirus vectors is widely used. Other insect vector systems include, for example, the expression plasmid pIZ/V5-His (InVitrogen, San Diego, Calif., USA) and other variants of the pIZ/V5 vectors encoding other tags and selectable markers. Insect cells are readily transfectable using lipofection reagents, and there are lipid-based transfection products specifically optimized for the transfection of insect cells (for example, from PanVera (Madison, Wis., USA)).

Host Cells Useful According to the Invention

Any cell into which recombinant vectors carrying an interferon antagonist gene or variant thereof may be introduced and wherein the vectors are permitted to drive the expression of interferon anatagonist protein sequences is useful according to the invention. Vectors suitable for the introduction of interferon anatagonist protein-encoding sequences in host cells from a variety of different organisms, both prokaryotic and eukaryotic, are described herein above or known to those skilled in the art.

Host cells may be prokaryotic, such as any of a number of bacterial strains, or may be eukaryotic, such as yeast or other fungal cells, insect or amphibian cells, or mammalian cells including, for example, rodent, simian or human cells. Cells expressing interferon anatagonist proteins of the invention may be primary cultured cells, for example, primary human fibroblasts or keratinocytes, or may be an established cell line, such as NIH3T3, 293T or CHO cells. Further, mammalian cells useful for expression of interferon anatagonist proteins of the invention may be phenotypically normal or oncogenically transformed. It is assumed that one skilled in the art can readily establish and maintain a chosen host cell type in culture, Antibodies According to the Invention The invention provides for antibodies directed to different interferons, Antibodies can be made using standard protocols known in the art (see, for example, Antibodies: A Laboratory Manual ed. by Harlow and Lane (Cold Spring Harbor Press: 1988)). A mammal, such as a mouse, hamster, or rabbit can be immunized with an immunogenic form of the interferon. Immunogens for raising antibodies are prepared by mixing the polypeptides (e.g., isolated recombinant polypeptides or synthetic peptides) with adjuvants. Alternatively, interferon proteins or peptides are made as fusion proteins to larger immunogenic proteins. Polypeptides can also be covalently linked to other larger immunogenic proteins, such as keyhole limpet hemocyanin. Alternatively, plasmid or viral vectors encoding interferon polypeptide or interferon peptides can be used to express the polypeptides and generate an immune response in an animal as described in Costagliola et al., 2000, J. Clin. Invest. 105:803-811, which is incorporated herein by reference in its entirety. In order to raise antibodies, immunogens are typically administered intradermally, subcutaneously, or intramuscularly to experimental animals such as rabbits, sheep, and mice. In addition to the antibodies discussed above, genetically engineered antibody derivatives can be made, such as single chain antibodies (Fv, Fab, scFV, F(ab)2, VH, VL). In a preferred embodiment, the immunogen is administered to rabbits.

The progress of immunization can be monitored by detection of antibody titers in plasma or serum. Standard ELISA, flow cytometry or other immunoassays can also be used with the immunogen as antigen to assess the levels of antibodies. Antibody preparations can be simply serum from an immunized animal, or if desired, polyclonal antibodies can be isolated from the serum by, for example, affinity chromatography using immobilized immunogen.

To produce monoclonal antibodies, antihody-producing splenocytes can be harvested from an immunized animal and fused by standard somatic cell fusion procedures with immortalizing cells such as myeloma cells to vield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hlybridoma cells can be screened immunochemically for production of antibodies specifically reactive with interferon polypeptide or peptides, and monoclonal antibodies isolated from the media of a culture comprising such hybridoma cells.

The term "antibody" as used herein is intended to include antibody fragments, which are also specifically reactive with one of the subject polypeptides or peptides of the invention. Antibodies can be fragmented using conventional techniques and the fragments screened for utility in the same manner as described above for whole antibodies For example, F(ab)2 fragments can be generated by treating antibody with pepsin. The resulting F(ab)2 fragment can be treated to reduce disulfide bridges to produce Fab fragments. The antibody of the present invention is further intended to include bispecific, single-chain, and chimeric and humanized molecules having affinity for a polypeptide or peptide of the invention conferred by at least one CDR region of the antibody. In preferred embodiments, the antibody further comprises a label attached thereto and able to be detected, e.g., the label can be a radioisotope, fluorescent compound, cherniluminescent compound, enzyme, or enzyme co-factor.

Antibodies can be used, e.g., to monitor protein levels in an individual for determining, e.g., whether a subject has a immune disease or condition, that is associated with an aberrant amount of peptide in tissue biopsies or allowing determination of the efficacy of a given treatment regimen for an individual afflicted with such a disorder. The level of the interferons of the invention may be measured in bodily fluids, such as in blood samples. Another application of antibodies of the present invention is in the immunological screening of bioavailable interferon in the blood samples of patients afflicted with a disease to be treated as disclosed herein. In another embodiment of the invention, the anti-interferon antibody is an interferon antagonist.

Interferon Antagonist Protein Expression

In order to express a biologically active protein, the nucleotide sequence encoding the protein of interest or its functional equivalent, is inserted into an appropriate expression vector, i.e., a vector which contains the necessary elements for the transcription and translation of the inserted coding sequence. The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. Methods which are well known to those skilled in the art can be used to construct expression vectors containing a protein-encoding sequence and appropriate transcriptional or translational controls. These methods include in vivo recombination or genetic recombination. Such techniques are described in Ausubel et al., supra and Sambrook et al., supra.

A variety of expression vectorihost systems may be utilized to contain and express a protein product of a candidate gene according to the invention. These include but are not limited to microorganisms such as bacteria transformed with recombinant bacteriophage, plasmid or cosmid DNA expression vectors; yeast transformed with yeast expression vectors, insect cell systems infected with virus expression vectors (e.g., baculovirus); plant cell systems transfected with virus expression vector (e.g., cauliflower mosaic virus, CaMV; tobacco mosaic virus, TMV) or transformed with bacterial expression vectors (e.g., Ti or pBR322 plasmid); or animal cell systems.

In bacterial systems, a number of expression vectors may be selected depending upon the use intended for the protein of interest. For example, when large quantities of a protein are required for the production of antibodies, vectors which direct high level expression of fusion proteins that are readily purified may be desirable. Such vectors include, but are not limited to, the multifunctional *E. coli* cloning and expression vectors such as Bluescript® (Stratagene, La Jolla, Calif., USA), in which the sequence encoding the protein of interest may be ligated into the vector in frame with sequences encoding the amino-terminal Met and the subsequent 27 residues of β-galactosidase so that a hybrid protein is produced; pm vectors (Van Heeke & Schuster, 1989, J. Biol. Chem. 264: 5503); and the like. Pgex vectors (Promega, Madison, Wis., USA) may also be used to express foreign polypeptides as fusion proteins with GST. In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al. (supra) and Grant et al., 1987, Methods in Enzymology 153:516.

In cases where plant expression vectors are used, the expression of a sequence encoding a protein of interest may be driven by any of a number of promoters. For example, viral promoters such as the 35S and 19S promoters of CaMV (Brisson et al., 1984, Nature 310:511) may be used alone or in combination with the omega leader sequence from TMV (Takamatsu et al., 1987, EMBO J. 6:307). Alternatively, plant promoters such as the small subunit of RUBISCO (Coruzzi et al., 1984, EMBO J. 3:1671; Broglie et al., 1984, Science, 224:838); or heat shock promoters (Winter J. and Sinibaldi R. M., 1991, Results Probi. Cell. Differ. 17:85) may be used. These constructs can be introduced into plant cells by direct DNA transformation or pathogen-mediated transection. For reviews of such techniques, see Hobbs S. or Murry L. E. in McGraw Hill Yearbook of Science and Technology (1992) McGraw Hill New York N.Y., pp 191-196 or Weissbach and Weissbach (1988) Methods for Plant Molecular Biology, Academic Press, New York, pp 421-463.

An alternative expression system which could be used to express a protein of interest is an insect system. In one such system, *Autographa californica* nuclear polyhedrosis virus (AcNPV) is used as a vector to express foreign genes in *Spodoptera frugiperda* cells or in *Trichoplusia larvae*. The sequence encoding the protein of interest may be cloned into a nonessential region of the virus, such as the polyhedrin gene, and placed under control of the polyhedrin promoter. Successful insertion of the sequence encoding the protein of interest will render the polyhedron gene inactive and produce recombinant virus lacking coat protein coat. The recombinant viruses are then used to infect *S. frigoerda* cells or *Trichoplusia larvae* in which the protein of interest is expressed (Smith et al., 1983., J. Virol. 46:584; Engelhard et al., 1994, Proc. Nat. Acad. Sci. USA 91:3224).

In mammalian host cells, a number of viral-based expression systems may be utilized such as vaccinia virus, adenoviruses and retroviruses and the like. In cases where an adenovirus is used as an expression vector, a sequence encoding the protein of interest may be ligated into an adenovirus transcription/translation complex consisting of the late promoter and tripartite leader sequence. Insertion in a nonessential E1 or E3 region of the viral genome will result in a viable virus capable of expressing in infected host cells (Logan and Shenk, 1984, Proc. Natl. Acad. Sci. USA 81:3655). In addition, transcription enhancers, such as the rous sarcoma virus (RSV) enhancer, may be used to increase expression in mammalian host cells.

Specific initiation signals may also be required for efficient translation of a sequence encoding the protein of interest. These signals include the ATG initiation codon and adjacent sequences. In cases where the sequence encoding the protein, its initiation codon and upstream sequences are inserted into the most appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf et al., 1994, Results Probl. Cell. Differ., 20:125; Bittner et al., 1987, Methods in Enzymol. 153:516).

In addition, a host cell strain may be chosen for its ability to modulate the expression of the inserted sequences or to process the expressed protein in the desired fashion. Such modifications of the polypeptide include but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stabie expression is preferred. For example, cell lines which stably express a foreign protein may be transformed using expression vectors which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clumps of stably transformed cells can be expanded using tissue culture techniques appropriate to the cell type.

Any number of selection systems may be used to recover transformed cell lines. These include, but are not limited to, the herpes simplex virus thymidine kinase (Wigler et al., 1977, Cell 11:223) and adenine phosphoribosyltransferase (Lowy et al., 1980, Cell 22:817) genes which can be employed in tk- or aprt-cells, respectively. Also, antimetabolite, antibiotic or herbicide resistance can be used as the basis for selection; for example, dhfr which confers resistance to methotrexate (Wigler et al., 1980, Proc. Natl. Acad. Sci. USA 77:3567); npt, which confers resistance to the aminoglycosides neomycin and G-418 (Colbere-Garapin et al., 1981, J. Mol. Biol., 150:1) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman and Mulligan, 1988, Proc. Natl. Acad. Sci. 85:8047). Recently, the use of visible markers has gained popularity with such markers as anthocyanins, B glucuronidase and its substrate, GUS, and luciferase and its substrate, luciferin, being widely used not only to identify transformants, but also to quantify the amount of transient or stable protein expression attributable to a specific vector system (Rhodes et al., 1995, Methods. Mol. Biol. 55:121).

Modifications of Interferon Antagonist Proteins

When needed, the IFN binding proteins, and their formulation, can be modified. Such modifications are intended to fall within the scope of the present invention, and examples are provided below.

Multimerization

For various reasons that include increasing IFN binding affinity and/or beneficially altering metabolism and excretion, the IFN binding proteins can be linked together as homomultimers (e.g., as in FIG. 6A) or as heteromultimers (e.g., as in FIG. 6B) for example by cysteine bridges (Moosmayer, D. et al., 1995, J. Interferon Cytokine Res. 15:1111-1115), other protein-protein interactions, and/or as fusion proteins coded for by linked genes. These general procedures are well known to those practiced in the art.

Blood Brain Barrier (BBB) Transport Enhancement

For the treatment of some diseases it may be desirable or necessary to enhance the ability of the interferon binding proteins to pass through the BBB. This can be accomplished by various modifications described in the literature (Poduslo, J. F. et al., 1994, Brain Res. Mol. Brain Res. 23:157-162; Triguero, D. et al., 1989, Proc. Natl. Acad. Sci. USA 86:4761-4765), e.g., catonization (Triguero, D. et al., 1991, J. Pharmacol. Exp. Ther. 258:186-192) or glycation (Poduslo, J. F. et al., 1994, Brain Res. Mol Brain Res. 23:157-162) including linkage as a fusion protein with an iron binding/transport protein (e.g., p97 (U.S. Pat. No. 5,981,194). The ability of transferrin to enhance the BBB uptake of other proteins has been taught by others (Shin, S. U. et al., 1995, Proc. Nati. Acad. Sci. USA 92:2820-2824). The use of human transferrin (Tf) to enhance the ability of a specific group of polypeptides to pass through the blood-brain barrier (BBB) is taught by U.S. Pat. Nos. 5,672,683, 5,182,107 and 5,527,527. The Tf polypeptide can be added to the fusion proteins of the present invention using standard procedures using, for example the Tf gene obtained from a human liver cDNA library (Clontech, Palo Alto, Calif., USA) using the following primers and standard procedures:

```
P1: TCTAGATGGTGTGCAGTGTCGGAGC     (SEQ ID NO: 3)
and

P2: CGTACGGAAAGTGCAGGCTTCCAG.     (SEQ ID NO: 4)
```

FIG. 6 presents examples of interferon binding proteins as fusion proteins with human transferrin along with the further modification of linkage through a flexible hinge region. A specific immunoglobin example of this type of linkage is described by Michaelsen et al (Michaelsen, T. E. et al., 1977, J. Biol. Chem. 252:883-889).

Reducing Immunogenicity and Improving Phamacokinetics

Additional modifications could, for example, include addition of polyethylene glycol (PEG) and/or other moieties (Hershfield, M. S. et al., 1991, Proc. Natl. Acad. Sci. USA. 88:7185-7189). This modification has been shown to reduce the ability of the immune system to mount an immune response (flershfield, M. S. et al., 1991, Proc. Natl. Acad. Sci. USA 88:7185-7189) and to increase serum half-life partly by increasing overall molecule size.

Modification for Alternate Modes of Administration

Polyethylene glycol (PEG) and other functionally similar molecules can also be used as part of the formulation to provide the advantage of time-release and/or reduced site of injection inflammation (Hershfield, M. S. et a)., 1991, Proc. Natl. Acad. Sci. USA 88:7185-7189; Somack, R. et al., 1991, Free Radic. Res. Commun. 12-13:553-562). Other examples of modifications would include preparation as an aerosol for transpulmonary delivery (U.S. Pat. No. 5,558,085) modifications for oral delivery (U.S. Pat. No. 6,153,211) and/or modifications to improve intravenous (IV), subcutaneous (SC), nasal, or intramuscular (IM) routes of delivery.

Selection of Dose and Timing of Administration

Dosage, Formulation and Administration

The therapeutic agent of the invention can be used in a composition that is combined with a pharmaceutically acceptable carrier. Such a composition may also contain diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The composition may also contain other agents, which either enhance the activity of the composition, or compliment its activity or use in treatment, or maintain the activity of the therapeutic agent in storage. Such additional factors and/or agents may be included in the composition to produce a synergistic effect or to minimize side effects. Additionally, administration of the composition of the present invention may be administered concurrently with other therapies.

Administration of the therapeutic agent of the present invention can be carried out in a variety of conventional ways, such as oral ingestion, inhalation, topical application or cutaneous, subcutaneous, intraperitoneal, parenteral or intravenous injection.

The compositions containing the therapeutic agent of the present invention can be administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent, i.e., carrier or vehicle.

Modes of administration of the therapeutic agent of the present invention include intravenous, intramuscular, intraperitoneal, intrasternal, subcutaneous and intraarticular injection and infusion. Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (e.g., glycerol, propylene glycol, polyethylene glycol and the like), carboxymethylcellulose and suitable mixtures thereof vegetable oils (e.g., olive oil) and injectable organic esters such as ethyl oleate. Proper fluidity may be maintained, for example, by the use of coating materials such as lecithin, by the maintenance of the required particle size in the case of dispersions and by the use of surfactants. These compositions may also contain adjuvants such as preservatives, wetting agents, emulsifying agents and dispersing agents, and/or compounds to shield the immunogenic determinant of the therapeutic agent. Prevention of the action of microorganisms may be improved by the inclusion of various antibacterial and antifungal agents such as paraben, chlorobutanol, phenol sorbic acid and the like. It may also be desirable to include isotonic agents such as sugars, sodium chloride and the like. Prolonged absorption of an injectable pharmaceutical form may be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations may be sterilized, for example, by filtration through a bacterial-retaining filter or by incorporating sterilizing agents in the form of sterile solid compositions which can be dissolved or dispersed in sterile water or other sterile injectable media just prior to use.

The formulations include those suitable for oral, rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose dose or multi-dose containers. Extemporaneous injection solutions and suspensions may be prepared from sterile powders, granules and tablets of the kind previously described.

When a therapeutically effective amount of the therapeutic agent of the present invention is administered orally, the composition of the present invention will be in the form of a tablet, capsule, powder, solution or elixir. When administered in tablet form, the composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the composition may further contain physiological saline solution, dextrose or other saccharide solution, or glycols such as ethylene glycol, propylene glycol or polyethylene glycol. When administered in liquid form, the composition contains from about 0.5 to 90% by weight of protein of the present invention, and preferably from about 1 to 50% protein of the present invention.

When a therapeutically effective amount of the therapeutic agent of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art, The composition of the present invention may also contain stabilizers, preservatives, buffers, antioxidants, or other additives known to those of skill in the art.

Topical administration, in which the composition is brought in contact with tissue(s), may be suitable for sarcoidosis of the skin. By "contacting" is meant not only topical application, but also those modes of delivery that introduce the composition into the tissues, or into the cells of the tissues.

Use of timed release or sustained release delivery systems are also included in the invention, Such systems are highly desirable in situations where the patient is debilitated by age or the disease course itself, or where the risk-benefit analysis dictates control over cure.

A sustained-release matrix, as used herein, is a matrix made of materials, usually polymers, which are degradable by enzymatic or acid/base hydrolysis or by dissolution. Once inserted into the body, the matrix is acted upon by enzymes and body fluids. The sustained-release matrix desirably is chosen from biocompatible materials such as liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The amount of the therapeutic agent of the present invention in the pharmaceutical composition of the present invention will depend upon the nature and severity of the condition being treated, and on the nature of prior treatments, which the patient has undergone. Ultimately, the attending physician will decide the amount of the therapeutic agent of the present invention with which to treat each individual patient. Initially, the attending physician will administer low doses of the therapeutic agent of the present invention and observe the patient's response. Larger doses of may be administered until the optimal therapeutic effect is obtained for the patient, and at that point the dosage is not increased further.

The duration of intravenous therapy using the pharmaceutical composition of the present invention will vary, depending on the severity of the disease being treated and the condition and potential idiosyncratic response of each individual patient. It is contemplated that the duration of each application of the therapeutic agent of the present invention will be in the range of 12 to 24 hours of continuous intravenous administration. Ultimately the attending physician will decide on the appropriate duration of intravenous therapy using the pharmaceutical composition of the present invention.

The amount of an antibody antagonist administered is between 1 and 100 mg/kg. The preferred route of administration of an antibody antagonist is intravenous administration to infant and adult subjects. The preferred route of administration to fetal subjects is by intravenous administration to the mother followed by transplacental transport. Alternatively antibody antagonists can be administered by intramuscular and subcutaneous routes. When an antagonist is delivered transplacentally, the calculation of the dose is based on the maternal weight.

The antagonist is administered to patients having Down syndrome preferably at the time when the central nervous system is developing most rapidly. The preferred period of administration is from a gestational age of 24 weeks onwards until a post natal age of about 2 years. Even though some proliferation of neurons takes place during weeks 8-18, it is not critical that an antagonist be administered to a human subject prior to week 20-24 of gestational age because the synaptic connections between the neurons are not formed until week 20. Brandt, I., 1981, J, Perinat. Med. 9:3. The administration of the antagonist to patients having Alzheimer's disease should commence at the time that the diagnosis of probable Alzheimer's disease is first made and continue there after. In middle age, subjects having Down syndrome develop a dementia having an anatomical pathology which is identical to Alzheimer's disease (Mann, D. M. A., 1988, Mech. Aging and Develop. 43:99-136). Thus, the administration of the antagonist to Down syndrome patients can be continued throughout the life of the patient, as Down syndrome patients are at risk for Alzheimer's disease ab initio.

The frequency of administration is determined by the circulation time of the antagonist, which can be determined by direct measurement by methods well known to those skilled in the art.

In an alternative embodiment of the invention, the administration of interferon antagonists is replaced by the extracorporeal treatments of the subject's blood to remove circulating interferon, such as is described in U.S. Pat. No. 4,605,394.

Diseases to be Treated by Interferon Antagonists of the Invention

Appropriate pharmacological preparations of the compositions of the present invention are useful for the treatment and prevention of diseases where increased synthesis of, or responsivity to, the interferons is involved. Examples of these are Down syndrome, Alzheimer's disease, HIV infection, autoimmune disease, transplant rejection, and infant encephalitis.

Down's Syndrome:

The tissues of a Down syndrome individual displays increased responsivity to both IFN-γ and IFN-α. In addition, there exist significant similarities between the side effects of interferon therapy and Down syndrome pathologies (Maroun, L. E. et al., 1998, Down syndrome: Research and Practice 5:143-147; U.S. Pat. No. 5,780,027).

Alzheimer's Disease:

The presence of trisomy 21 (Down syndrome) cells (Geller, L. N. et al., 1999, Neurobiol. Dis. 6:167-179) and an increase in interferon levels (Yamada, T. et al., 1994, Neurosci. Lett. 181:61-64) are both reported to be present in the Alzheimer's disease brain. Further, the interferons are involved in both the synthesis and the processing of a brain protein (APP) that plays a central role in the development and progression of AD associated dementia (Blasko, I. et al., 1999, Faseb. J. 13:63-68).

HIV Infection:

Increased levels of both IFN-γ and IFN-α have been demonstrated in HIV infected patients of various ages (Fuchs, D. et al., 1989, J. Acquir. Immune Defic. Syndr. 2:158-162; Minagawa, T. et al., 1989, Life Sci. 45:iii-vii; Rossol, S. et al., 1989, J. Infect. Dis. 159:815-821). Clinical data suggests that decreasing the IFN activity improves the HIV infected patient's prognosis (Fall, L. S. et al., 1995, Biomed. Pharmacother. 49:422-428; Gringeri, A. et al., 1994, J. Acquir. Immune Defic. Syndr. 7:978-988.; Gringeri, A. et al., 1995, Cell Mol. Biol. (Noisy-le-grand) 41:381-387; Gringeri, A. et al., 1996, J. Acquir. Immune Defic. Syndr. Hum. Retrovirol. 13:55-67.; Gringeri, A. et al., 1999, J. Acquir. Immune Defic. Syndr. Hum. Retrovirol. 20:358-370). The method used these studies is taught by U.S. Pat. No. 6,093,405. This method is both unreliable (Fall, L. S. et al., 1995, Biomed. Pharmacother. 49:422-428; Gringeri, A. et a., 1994, J. Acquir. Immune Defic. Syndr. 7:978-988; Gringeri, A. et al., 1995, Cell Mol. Biol. (Noisy-le-grand) 41:381-387; Gringeri, A. et al., 1996, J. Acquir. Immune Defic. Syndr. Hum. Retrovirol. 13:55-67; Gringeri, A. et al., 1999, J. Acquir. Immune Defic. Syndr. Hum. Retrovirol. 20:358-370) and irreversible.

Administration of the pharmacological compositions described herein is a significant improvement in this method as it provides for predictable and controllable IFN antagonist levels that can be adjusted according to patient needs and treatment can be discontinued in the event IFN activity falls below safe levels.

Encephalitis in Infants:

Encephalitis in infants can be caused by viral infection (e.g., herpes infection (Dussaix, E. et al., 1985, Acta Neurol. Scand. 71:504-509) or have unknown origin (e.g., Aicardi-Goutieres Syndrome (Akwa, Y. et al., 1998, J. Immunol. 161:5016-5026). Both of these conditions are associated with increased levels of IFN (Akwa, Y. et al., 1998, J. Immunol. 161:5016-5026; Dussaix, E. et al., 1985, Acta Neurol. Scand. 71:504-509). In the case of Aicardi-Goutieres Syndrome and animal models of it, elevated levels of IFN may be the primary cause of the disease.

Autoimmune Disease:

Elevated IFN levels play a central role in the development and progression of various autoimmune diseases (Le Page, C. et al., 2000, Rev. Immunogenet. 2:374-386). Thus, it is expected that individuals suffering from these diseases would benefit by use of the present invention.

Transplant Rejection:

Interferon has been shown to play an important role in the immunological rejection of transplanted cells, tissues and/or organs (see, Cytokines and Autoimmunity, O'Shea, J. J., Ma, A., Lipsky, P., Nature Rev. Immunol, 2(1):37-45 (2002)).

Thus, it is expected that individuals suffering from these diseases would benefit by use of the present invention.

The above descriptions are by example only and are not intended to limit the present invention's usefulness. Indeed it is immediately obvious to one skilled in the art that in IFNs play an important role in various other diseases. These diseases are considered to be within the scope of the present invention. The described compositions would be useful for the treatment of all diseases where interferon hyper-production or hyper-responsivity is involved. Alzheimer's disease, HIV infection, Down syndrome, autoimmune disease, and infant encephalitis are examples of such diseases.

Animal Models of the Diseases to be Treated According to the Invention

Animal models of disease are useful for determining the efficacy of treatment using the pharmaceutical compositions according to the invention. For example, an animal model for multiple sclerosis is experimental autoimmune encephalomyelitis (EAE), which can be induced in a number of species, e.g., guinea pig (Suckling et al., 1984, Lab. Anim. 18:36-39), Lewis rat (Feurer et al., 1985, J. Neuroimmunol. 10:159-166), rabbits (Brenner et al., 1985, Isr. J. Med. Sci. 21:945-949), and mice (Zamvil et al., 1985, Nature 317:355-358).

There are numerous animal models known in the art for diabetes, including models for both insulin-dependent diabetes mellitus (IDDM) and non-insulin-dependent diabetes mellitus NIDDM). Examples include the non-obese diabetic (NOD) mouse (e.g., Li et al., 1994, Proc. Natl. Acad. Sci. USA. 91:11128-11132), the BB/DP rat (Okwueze et al., 1994, Am. J. Physiol. 266:R572-R577), the Wistar fatty rat (Jiao et al., 1991, Int. J. Obesity 15:487-495), and the Zucker diabetic fatty rat (Lee et al., 1994, Proc. Natl. Acad. Sci. USA. 91:10878-10882). There are also animal models for autoimmune thyroiditis (Dietrich et al., 1989, Lab. Anim. 23:345-352) and Crohn's disease (Dieleman et al., 1997, Scand. J. Gastroenterol. Supp. 223:99-104; Anthony et al., 1995, Int. J. Exp. Pathol. 76:215-224; Osborne et al., 1993, Br. J. Surg. 80:226-229).

Some representative animals models are included below.

Down Syndrome:

Trisomy 16 mouse: Gropp, A. et al., Cytogenet. Cell Genet. 14:42-62 (1975)

Partial trisomy 16 mouse: Davisson, M. T. et al. Prog. Clin. Biol. Res. 384:117-133 (1993)

Alzheimer's Disease.

Transgenic mice expressing beta-amyloid precursor protein [Games, D. et al., Nature, 9:373(6514):523-7(1995)]

Pathology of HIV Infection:

Retrovirus infected mice: Morse III, H. C. et al., AIDS 6:607-621 (1992)

Retrovirus infected cats: Podell, M. et al., J. Psychopharmacol. 14(3)-205-213 (2000)

Retrovirus infected monkeys: Rausch, D. M. et al., J. Leukoc. Biol. 65(4):466-474(1999)

Intracerebral HIV coat protein injection in rats, Glowa, J. R. et al., Brain Res. 570:49-53(1992)

Encephalitis in Infants:

Infantile encephalitis (Aicardi-Goutieres syndrome): IFN-α transgenic mice: Akwa, Y. et al., J. Immuno. 161:5016-5026 (1998)

Mouse Herpes simplex virus encephalitis: Mayding-Lamade, U. et al., Neurosci. Lett. 22; 248(I):13-16 (1998)

LCM virus enciphalitis in mice: Pfau, C. J. et al., J. Gen. Virol. 64(8):1827-1830 (1993)

Autoimmune Disease:

Diabetes: IFN-α transgenic mice [Steward, T. A. et al., Science 260:1942-46 (1993)

Systemic Lupus Erythematosus: NZB/W F1 mice: Jacob, C. O. et al., J. Exp. Med. 166(3):798-803 (1987)

Multiple Sclerosis: IFN-γ Transgenic mice: Corbin, J. G. et al., Mol. Cell, Neurosci. 7(5):354-370 (1996)

Transplant Rejections:

Canine renal allografts: Fuller, L. et al., Tissue Antigens 43:163-169 (1994)

These accepted animal model systems, or others known and accepted in the art to be representative of human disease, can be used to test the efficacy of therapeutic approaches using the interferon antagonist polypeptides and variants thereof according to the invention. Generally, this is accomplished by administering the polypeptide composition to an animal that has or can be induced to have the model disease corresponding to the human disease one aims to treat, and monitoring the disease status. The response to the administered composition is then monitored by measuring the amount of bioavailable interferon on the bloodstream using anyone of a number of immunological assays known in the art such ELISA or radioimmunoassays and the like. Disease status is monitored according to criteria established for the particular disease or disease model, and treatment is considered effective if one or more symptoms or markers of disease are decreased by 10% or more relative to animals not treated or relative to the same animal before treatment.

Model Embodiment of the Invention

One embodiment of the invention is exemplified and its operability is demonstrated by the experiments that are presented in Example 1 below. Briefly, normal female mice were crossed with double heterozygous males having Rb(6.16) and Rb(16.17) chromosomes. The females were injected with a mixture of rat monoclonal anti-IFN-γ (1500 neutralizing units) and rabbit polyclonal anti-IFN-α/β (1362 neutralizing units) interperitonally (i.p.) on days 8, 10, 12 and 14 of pregnancy. On day 17 the embryos were biopsied for cytogenetic classification, sacrificed and four gross parameters were measured and compared to the genetically normal littermates in order to assess relative development. Control groups consisted of untreated females and sham treated females which were given normal rabbit and rat serum γ globulin injections.

The four measured parameters were overall (crown-rump) length of the fetus, shape of the back (normally concave at birth), eye-closing (the eyes normally close shortly before birth) and fetal weight. The results of the comparison of each of the parameters from 17 untreated, 16 sham treated and 18 treated controls showed a statistically significant reduction in the growth retardation/maturation of the treated trisomy-16 fetal mice compared to their euploid littermates.

The fetuses from anti-IFN treated mothers had a mean weight decrease of −10.92% compared to a −21.47% decrease for the uninjected group (p=0.079) and a −30.46% decrease for the ns-IgG injected group (p=0.0003) relative to diploid littermates. The uninjected and ns-IgG) injected control groups were not statistically different from each other (p=0.174).

Example Treatment of Murine Trisomy-16 by a Interferon Antagonist

Materials and Methods

Animals and Mating. 6:16 Robertsonian translocation male (Rb[6.16]24Lub) and 17:16 Robertsonian translocation female (Rb[16.17]7Bnr) homozygotes were purchased from Jackson Laboratories, Bar Harbor, Me., USA. Mature (54 day) male offspring of these homozygotes (double heterozygotes) were mated to 8-10 wk old euploid, nulliparous, C3H/

HeJ females (Jackson Laboratories). Surgery was performed on day 17 or 18 to yield fetuses at the 17-25 mm stage (Theiler, K. (1972) In: The House Mouse, Springer, Berlin, Heidelberg, N.Y.). The last three days of gestation are when the morphologic characteristics (eye closure, back curvature and accelerated growth) can be quantified.

Injections. Intraperitoneal (IP) injections (0.25 cc) were begun on post-coitus day 8 (implantation occurs on day 5.5). Injections were given every 48 hours for a total of four injections per animal.

Rabbit polyclonal anti-mouse α/β IFN purified IgG (970 neutralizing units/mg of protein, cat. #25301), and rat monoclonal IgG1 anti-mouse γ IFN, (7,200 neutralizing units/mg, cat. #25001) were obtained from Lee Biomolecular Research Incorporated, San Diego, Calif. The anti-IFNs (supplied lyophilized from saline) were dissolved in sterile water-for-injection (Investage) at a concentration that would deliver 1500 neutralizing units of anti-γ and 1362 neutralizing units of anti-α/β IgG per injection. The expectation was that the IgG would reach the developing fetus through active IgG placental transfer (Guzman-Enriques, L. et al., 1990, J. Rheumatol., 17:52-56). Control injections delivered the same mg quantities of rat (Pierce Chemical Co., Rockford, Ill., USA, Cat. #31233X) and rabbit (Pierce Chemical Co., Rockford, Ill., USA, Cat. #31207X) non-specific IgG in an equivalent volume of sterile saline-for-injection (Abbott). A second control group consisted of uninjected mothers which were left undisturbed.

Fetus Processing, Fetuses, obtained by hysterectomy of mice sacrificed by cervical dislocation, were photographed, measured and fixed whole in Bouins fixative (Luna, L. G. (1968) In: Manual of Histologic Staining Methods of the Armed Forces Institute of Pathology, (3rd edition). The Blakiston Division, McGraw-Hill Book Company, New York). Prior to fixation, limb tissue was obtained and minced to provide fibroblast cultures for karyotyping. The fetal fibroblasts from the minced tissue were grown at 37° C. in EAGLE's Minimum Essential Media containing 20% fetal bovine serum, 2 mM glutamine, 100 units/ml of penicillin, and 100 μg/ml of streptomycin. After five days in culture, colchicine (Sigma Chemical Co., St. Louis, Mo., USA) was added to level of 1 μg/ml. One hour later, cells were collected, swelled in 25% media, and fixed in fresh methanol:acetic acid (3:1). Crown-to-rump length was measured immediately after the fetus was obtained by measuring the vertex-to-rump distance (without pressure on the fetus) while the fetus was floating in serum-free Minimum Essential Media. Except where otherwise noted, all statistical analyses were done using a two-tailed student's T-test.

Results and Discussion

Mice pregnant with trisomy 16 conceptuses were obtained by the mating of euploid nulliparous C3H/HeJ females with doubly heterozygous males. The males were also functionally euploid (i.e., they have a total of 40 chromosome arms) but they carried two Robertsonian translocation chromosomes (6.16 and 17.16), each with one chromosome #16 arm. The meiotic misdistribution of these translocation chromosomes results in a high frequency of trisomy 16 fetuses carrying a maternal acrocentric chromosome 16 and both paternal translocation pseudometacentric chromosomes. This genetic system has been described in detail (Gropp, A. et al., 1975, Cytogenet. Cell Genet, 14:42-62; Gearhart, J. D. et al., 1986, Brain Res. Bull. 16:789-801). Anti-IFN treated mothers received four IP injections of a cocktail of anti-α, β and γ IFN immunoglobulins. One control group of mothers was left unhandled and one was given comparable injections of non-specific IgG.

Mechanisms for the transfer of the IgG from mother-to-fetus and neonate vary widely from species to species. Generally, some combination of passive and active transport is involved; sequentially utilizing the yolk sac and placenta prior to birth, and the intestine postnatally, In the mouse system, maternal antibodies can initially be found in the fluid filling the blastocyst cavity (Brambell, F. W. R. 1966, The Lancet 7473). This may be due simply to passive diffusion, as this fluid generally resembles dilute maternal blood plasma. Shortly thereafter active transport of IgG class immunoglobulins via Fc receptors becomes primarily the function of the yolk sac. This function is later shared but, in rodents, never dominated by Fc mediated transfer of IgG across the placenta (Roberts, D. M. et al., 1990, J. Cell Biol. 111: 1867-1876). In the experiments presented here, mice were injected after day 5.5 because of the possibility that trophoblast interferon may play an important role at implantation (Roberts, R. M., 1991, BioEssays 13:121-126). In the mouse, injected polyclonal rabbit IgG has an expected half-life of approximately 5 days (Spiegelberg. H. L. & W. O. Weigle, 1965, J. Exp. Med. 121:323-337).

A total of 68 late stage fetuses with abnormal morphology were obtained from among 440 offspring of 143 doubly heterozygous male×C3H/HeJ female matings. Only fetuses that were both successfully karyotyped and from litters where euploid fetuses averaged greater than 17 mm in length (crown-to-rump [CRL]) are included in Table 3 and in all graphs. Fifty-one of a total of 68 trisomies met these criteria. In all cases, the return-toward-normal values are seen with or without the inclusion of unkaryotyped fetuses. For comparison, p values calculated with the unkaryotyped fetuses included are provided in brackets next to those calculated using only successfully karyotyped fetuses.

Figure 1B:
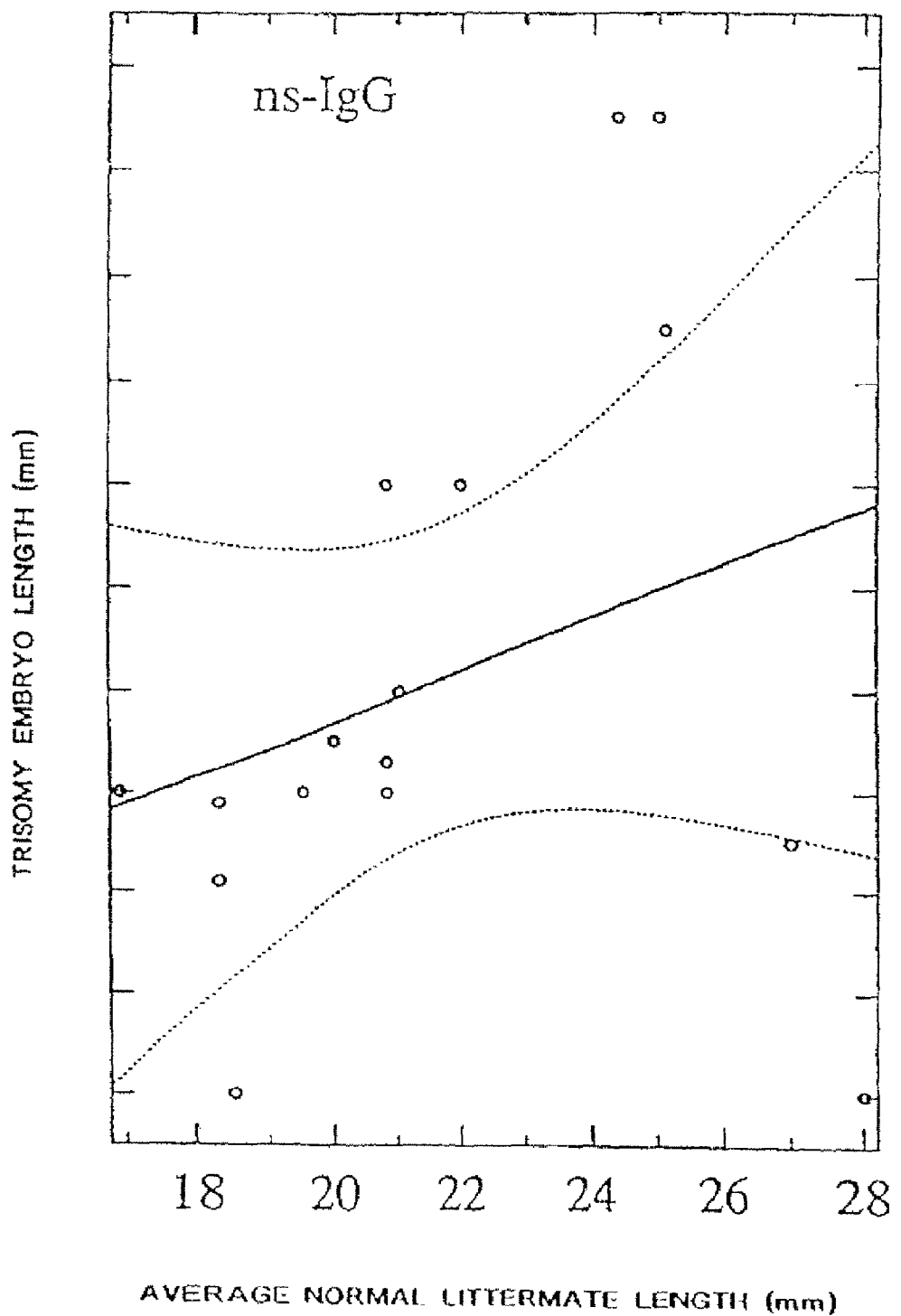
Figure 1C:
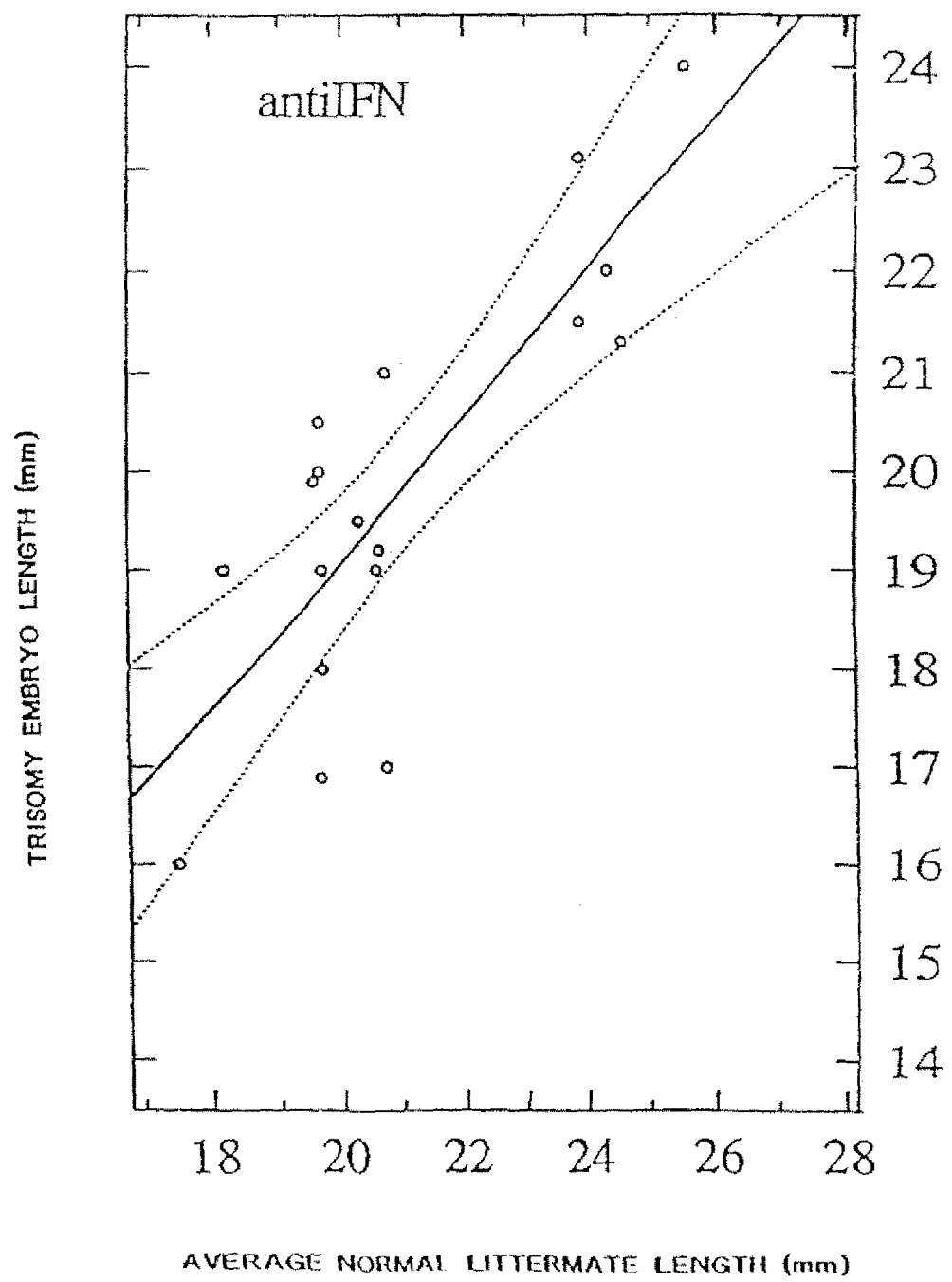

Growth Retardation. The growth retardation seen in the trisomy 16 fetus is quite variable. Nonetheless, the trisomic fetuses from the anti-IFN treated mothers showed a significant return-toward-normal growth when CRL length is plotted against the average length of the euploid littermates (FIG. 1). This analysis suggests that unlike the erratic growth of their counterparts from untreated mothers, the trisomy 16 fetuses from anti-IFN treated mothers were nearly keeping pace with the growth of their euploid littermates.

On average the trisomic fetuses from anti-IFN treated mothers showed a 5.6% decrease in length compared to a 15.28% decrease for the fetuses from non-specific IgG injected mothers (p=0.014 [0.0009]) and a 14.59% decrease for the fetuses from uninjected mothers (p=0.015 [0.010]). The two control groups were not statistically different from each other (p=0.879 [0.759]). The improvement in growth was seen consistently against both control groups and in all the fetus size groups (17-20 mm, 20-23 mm, >23 mm, Table 3).

A similar return-toward-normal growth was observed when the decrease in trisomy 16 fetal weights were analyzed. The fetuses from anti-IFN treated mothers had a mean weight decrease of −10.92% compared to a −21.47% decrease for the uninjected group (p=0.079 [0.095], NS) and a −30.46% decrease for the ns-IgG injected group (p=0.0003 [0.0026]). The two control groups were not statistically different from each other (p=0.174 [0.33]).

There were no detectable effects of the non-specific IgG or anti-IFN injections on the euploid fetuses. Growth of each trisomic fetus was measured against its normal littermates to avoid errors due to a missed estimate of gestational age. In these matings, the mean normal littermate length (MNLL) measured 17.17 mm CRL at gestational day 16.5, 19.39 mm CRL at day 17.5 and 23.94 mm CRL at day 18.5 (plug date=day 0.5 [Kaufman' 92]). There was no significant difference between the MNLL of the uninjected control group (gestational day) 18.5 (MNLL=23.944 [N=18, p=0.419]) or the IgG injected control group (MNLL=23.75 [N=6, p=0.706]), and the anti-IFN treated group (MNLL=23.333 [N=24]). There was also no significant difference between the MNLL of the two control groups (p=0.826).

Figure 2A:
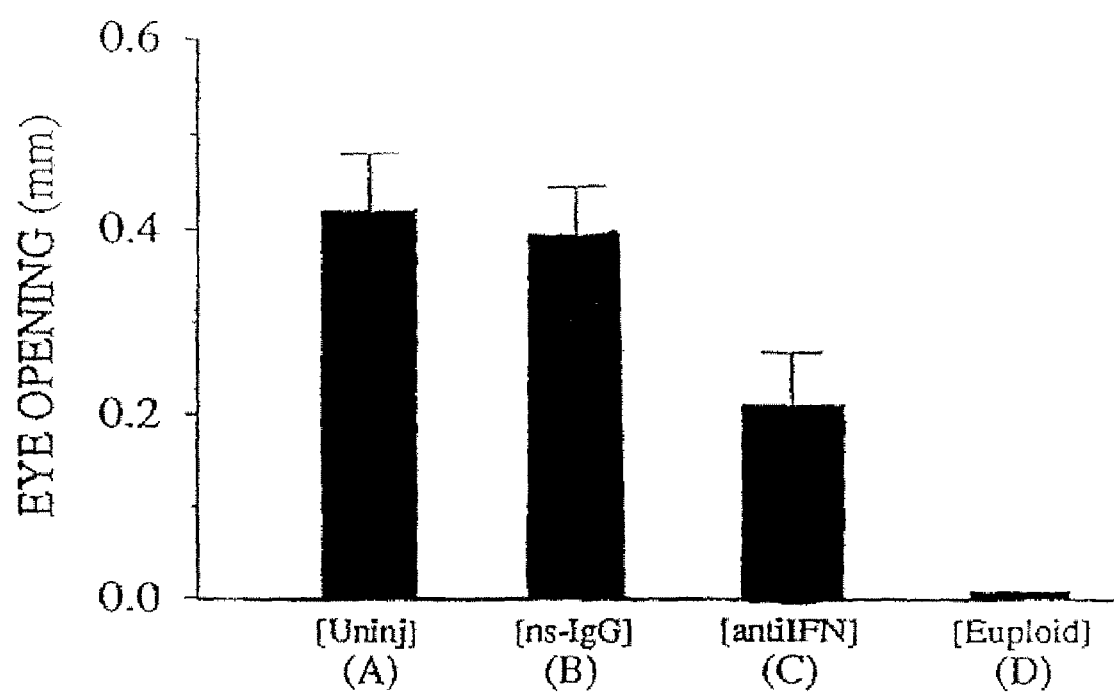
FIGS. 2A-2B. Morphometric analysis of the development in normal, Trisomy 16 treated and Trisomy 16 sham treated fetuses.

Eye Opening. Eye opening comparisons (FIG. 2A) were limited to fetuses from litters 17 mm to 23 mm in length. Prior to this stage all fetuses have open eyes. The eyes of fetuses from litters measuring 16.9-22.6 mm CRL obtained from anti-IFN treated mothers (N=13, mean=0.21 mm) had made significantly more progress toward closure than the eyes of comparably staged fetuses from untreated (N=11, mean=0.42 mm, p=0.019 [0.010]) and non-specific IgG injected mothers (N11, mean=0.40 mm, p=0.026 [0.046]). There was no significant difference in the eye openings of the uninjected and non-specific IgG injected control groups (p=0.746 [0.300]). Progress toward eye closure may be an all or nothing event. Thus, it may be equally significant that 7 of the 13 fetuses (54%) from anti-IFN treated mothers had eye openings that averaged less than 0.2 mm compared to 2 of 11 (18%) of those from untreated mothers and 2 of 11 (18%) of the comparable fetuses from non-specific IgG treated mothers.

There have been numerous mutations detected in the mouse that lead to open eyelids (Teramoto, S. et alt., 1988, Exp. Anim., 37:455-462). Most of these mutations show complete penetrance. However, some affect each eye variably and at least one phenotype can be reversed by a single maternal injection of steroids (Watney, M. J. & J. R. Miller, 1964, Nature 202:1029-1031). In addition, phenocopies of these mutants can be induced by common teratogens (Juriloff, D. M. et al., 1982, Can. J. Genet. Cytol., 25:246-254). The eyelid is lined with an active zone of cell growth (Kaufman, M. H., 1992, In: The Atlas of Mouse Development. Academic Press, Harcourt Brace Jovanovich, San Diego, Calif.), and these data indicate that the effect of the anti-IFN antibodies is to block cell growth inhibition of the interferon super-sensitive trisomy 16 cells lining the eyelids.

Figure 2B:
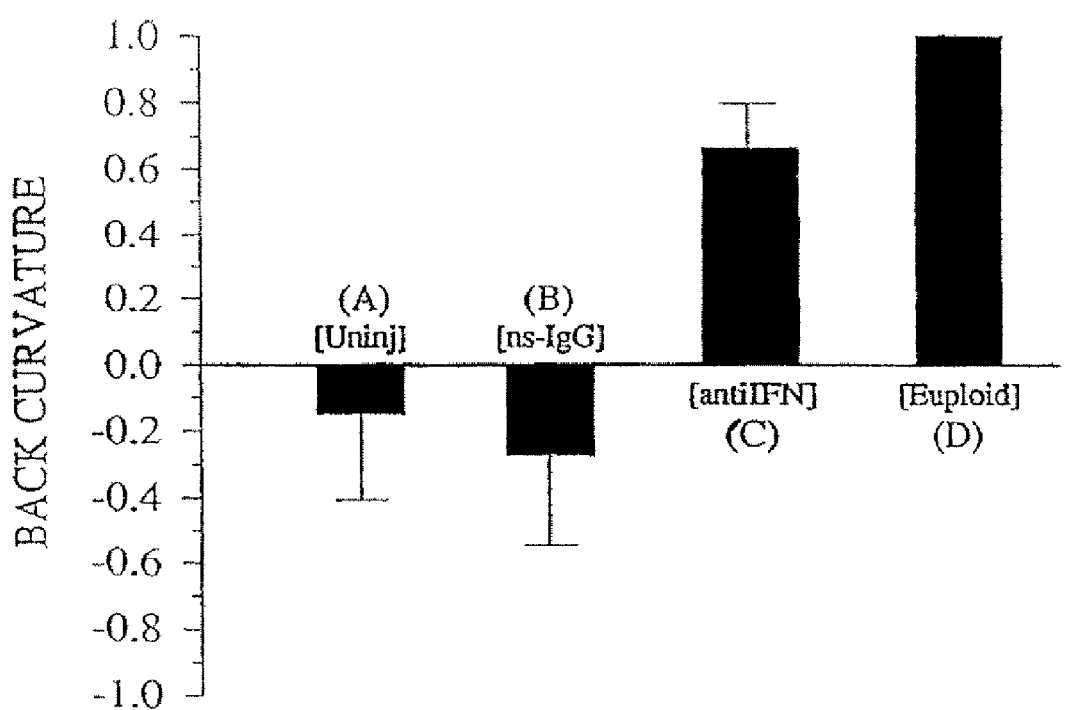
Figure 3:
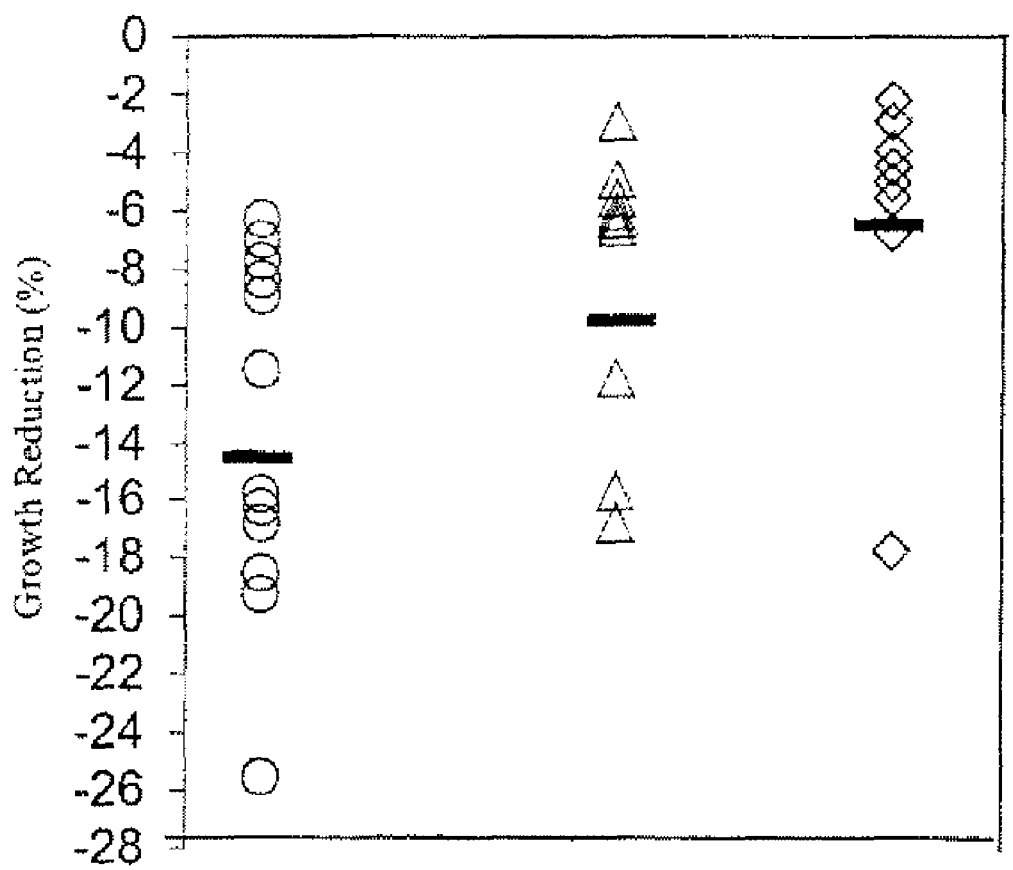
FIG. 3: Comparison of the improvement in trisomy 16 mouse fetus growth with a single (IFN-γ only) vs. double (IFN-γ plus IFN-α/β) receptor gene knockout. To produce the partial interferon receptor knockout trisomy (PIRKOT) mouse fetus, double IFN-γ+ IFN-α/β R−/− knockout males (B & K International) were mated to double translocation females [Rb(6,16)24LuB X Rb(16,17)7BNRFI, Jackson Labs]. Crown-to-Rump length was measured on day 15-19 fetuses. Growth retardation is expressed as a percent of mean euploid littermate length. Knockout of a single IFN-γ receptor gene was sufficient to significantly improve trisomy fetus growth rate (mean growth retardation: 9.15+/−1-49%, N=9, p=0.043). However, the double knockout was measurably more effective (mean growth retardation: 6.81+/−1.6%, N=8, p=0.008).

Back Curvature. One of the most striking effects of the maternal anti-IFN treatment was the return-toward-normal of the curvature of the trisomy 16 fetus back which is frequently rounded at later stages where a concave curvature is expected. Back curvature comparisons (FIG. 2B) are restricted to fetuses from litters greater than 20 mm in length because both euploid and trisomic fetuses are expected to have rounded backs prior to the 20 mm stage (Theiler, K., 1972, In: The House Mouse, Springer, Berlin, Heidelberg, N.Y.). Back curvature was assessed by a double-blind study in which three individuals scored a rounded back as a −1, a flat back as a 0 and a convex (normal) back as a +1. There was good agreement between the scores of the three individuals (correlations ranged from 0.80 to 0.92). The mean of the three evaluations was used for comparisons.

There was no significant difference in the back curvature scores of the trisomic fetuses from uninjected and non-specific IgG injected control mothers (p=0.8236 [0.3424]). The trisomic fetuses from anti-IFN treated mothers (N=10, mean=+0.66) showed a significant return-toward-normal back curvature when compared to fetuses from untreated mothers (N=9, mean=−0.18, p=0.009 [0.009]) and the comparable fetuses from non-specific IgG treated animals (N=11, mean=−0.27, p=0.008 [0.003]).

One hundred fifty fetuses whose eyes, back, and length, appeared normal were also karyotyped (75 control and 75 anti-IFN treated). A 24 mm fetus was one of two fetuses discovered to be trisomy in this screen. A second fetus (10 mm CRL) was also found in a litter from an anti-IFN treated mother and was essentially indistinguishable from its euploid littermates. LEGEND, Table 1: Compilation of data on karyotyped trisomy 16 fetuses.

(A) Mean length of normal littermates (mm, CRL); (B) Length of trisomic fetus (mm, CRL); (C) Change in trisomic fetus length relative to its normal littermates (%); (D) Average weight of normal littermates (gm); (E) Weight of trisomy fetus (gms); (F) Opening of the eyes (mm); (G) Average back curvature scores of three individuals, +1=normal concave, 0=flat, −1=rounded.

Example Construction of a Recombinant Interferon Antagonist Comprising Human Interferon α/β and γ Receptor Domains A gene encoding a fusion protein is constructed using a Glutamine-S-transferase containing expression plasmid pAcGHLT-B (PharMingen, San Diego, Calif., USA). The interferon binding domain of the human α/β interferon receptor is obtained by Nco I endonuclease digestion of plasmid p23, available from deposit No. ATCC 65007, and isolation of the 1177 bp fragment. This fragment is inserted into the Nco I site of pAcGHLT-B to yield pAcGST-23. The interferon binding domain of the human γ interferon receptor is obtained by Dsa I and Nsp I endonuclease digestion of the plasmid pUCLGRIF 16, available from deposit No. ATCC 59873, and isolation of the 603 bp fragment. A Pst I-Sma I digest of pAcGST-23 is used to remove a portion of the multiple cloning site located 3' of the gene encoding the α/β interferon receptor domain and the Dsa I/Nsp I fragment of pUCLGRIF 16 is inserted to yield pAcGST-23-γr. The translation product of the resultant construct, GST-α/β-γ, contains the following domains: GST-thrombin protease site-15 amino acid leader-α/β interferon receptor domain-6 amino acid spacer-γ interferon receptor domain.

A recombinant baculovirus is constructed containing the pAcGST-23-γr operably linked to the polyhedrin promoter, suitable host cells are infected and the resultant fusion protein isolated by an anti-GST affinity absorption techniques well known in the field. See, e.g., U.S. Pat. No. 4,745,071 and U.S. Pat. No. 4,879,236 to Smith et al. The isolated fusion protein is hydrolyzed with thrombin to yield the recombinant α/β-γ receptor.

Cloning of Vaccinia IFN Antagonist Genes

Viral DNA is extracted directly from live Vaccinia virus (ATCC Cat. No. VR-1354, WR Strain) using a QIAampDNA Mini Kit (Qiagen, Hilden , Germany, Cat. No. 51304). The DNA is then used as template for PCR amplification of the complete or truncated genes. The primers, based on the published gene sequences (B8R, GenBank Accession #AFO162273; B18R, GenBank Accession #D90076) are:

```
B8R P1:   ATGAGATATATTATAATTC        (SEQ ID NO: 5)
B8R P2:   TCATTAGTTAAATTTTCTCTTG     (SEQ ID NO: 6)
B18R P1:  AGTTACGCCATAGACATCGAA      (SEQ ID NO: 7)
B18R P2:  TCATTACTCCAATACTACTGTAGT   (SEQ ID NO: 8)
```

Figure 4:
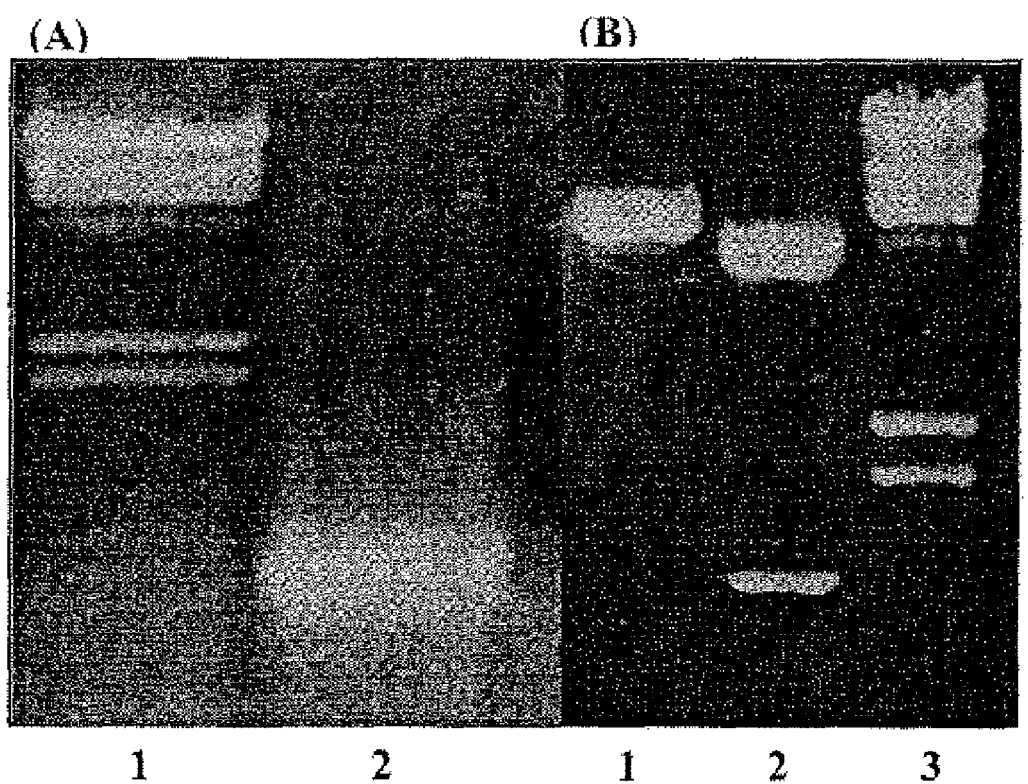
FIG. 4: Steps in the Cloning of Vaccinia IFN Inhibitor Genes.
Figure 5:
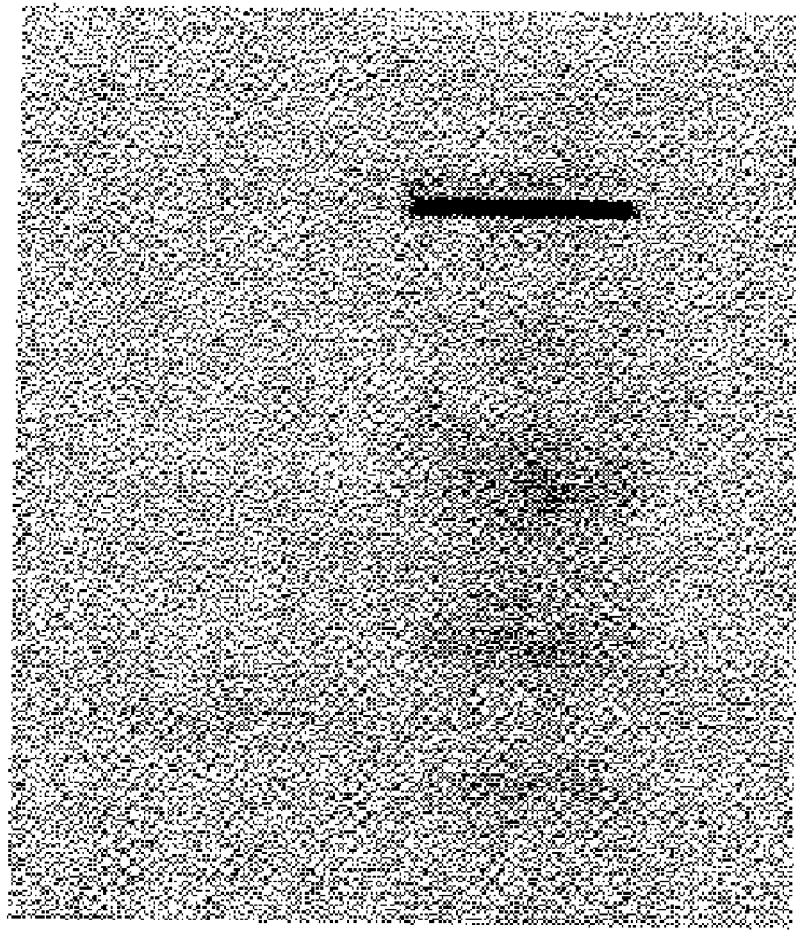
FIG. 5: Truncated human interferon γ receptor gene isolation. The human IFN-γ receptor gene is, by example, here isolated by PCR amplification from a thymus cDNA library (Clontech, Palo Alto, Calif., USA) for PCR subcloning into expression plasmids using the following primers: P1:ATG-GCTCTCCTCTTTCTCCTA (SEQ ID NO: 1), P2:TCTA-GAACCTTTTATACTGCTATTGAA (SEQ ID NO: 2. Lane 1: Truncated IFN-γ receptor gene. Lane 2: Lambda DNA markers.
Figure 6:
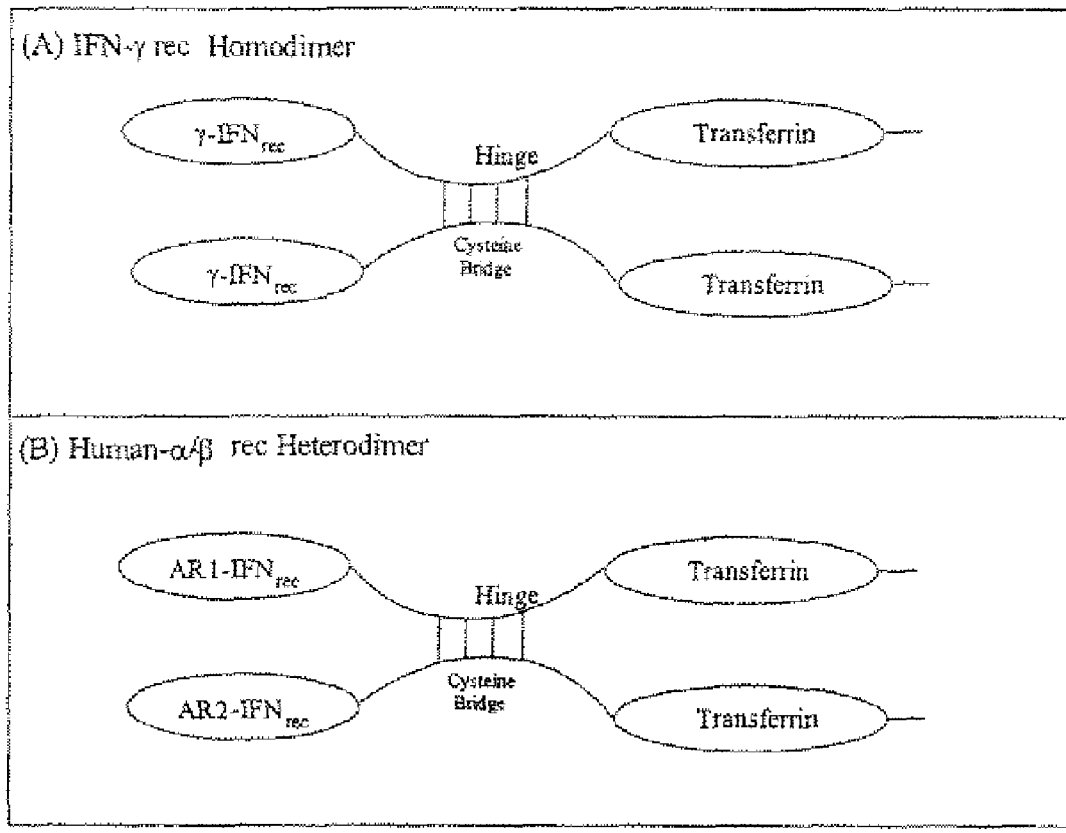
FIG. 6A: Example of a modified homodimer of the human IFN-γ receptor.
FIG. 6B. Example of a modified heterodimer with one copy each of both α-interferon receptor subunits (AR1 and AR2). The hinge region provides for two characteristics: (1) a flexible link to prevent receptor-Transferrin (Tf) mutual interference; and, (2) a signal to instruct the protein synthesis machinery of the eukaryotic cell to link two polypeptides together. The Tf provides the fusion protein with a longer serum half:life and the ability to be actively transported into the brain via the Tf receptors found lining the walls of the blood vessels of the brain.

After 35 PCR cycles (94.5° C. for 1 minute, 54.5° C. for 1 minute, 71.5° C. for 1.5 minutes) the incubation at 71.5° C. can be extended to 15 minutes to improve A overhang synthesis. The PCR product for the B18 (R gene is shown in FIG. 4. The PCR product can then be directly cloned into a mammalian expression plasmid (e.g., pcDNA4/HisMaxTOPO (In Vitrogen, Diego, Calif., USA)). Candidate plasmids can be screened by restriction endonuclease digestion. FIG. 4 shows the digestion profile of a plasmid isolate containing the B18R gene. Confirmation of the direction of the insert is accomplished by gene amplification using one primer for a site on the plasmid and an appropriate second primer chosen from those used for the original PCR amplification. The plasmids carrying the gene in the proper orientation are extracted from transformed 250 cc *E. coli* cultures using endotoxin free conditions (for example using a Qiagen Endo Free Plasmid Maxi Kit).

The present invention is not to be limited in scope by the specific embodiments described which were intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

The practice of the present invention will employ, unless otherwise indicated, conventional techniques of molecular biology, cell biology, microbiology and recombinant DNA techniques, which are within the skill of the art. Such techniques are explained fully in the literature. See, e.g., Sambrook, Fritsch & Maniatis, 1989, Molecular Cloning: A Laboratory Manual, Second Edition; Oligonucleotide Synthesis (M. J. Gait, ed., 1984); Nucleic Acid Hybridization (B. D. Harnes & S. J. Higgins, eds., 1984); A Practical Guide to Molecular Cloning (B. Perbal, 1984); (Harlow. E. and Lane, D.) Using Antibodies: A Laboratory Manual (1999) Cold Spring Harbor Laboratory Press; and a series, Methods in Enzymology (Academic Press, Inc.); Short Protocols In Molecular Biology, (Ausubel et al., ed., 1995). All patents, patent applications, and publications mentioned herein, both supra and infra, are hereby incorporated by reference in their entirety.

What is claimed is:

1. A method of reducing the incidence of pathological effects of a disease or decreasing the pathological effects of a disease, wherein said pathological effects are associated with excessive levels of one or more interferons in a patient suffering from said disease, comprising administering a therapeutically effective amount of one or more interferon binding proteins to said patient, wherein said one or more interferon binding proteins is selected from the group consisting of B18R, B8R, and a combination thereof.

2. The method of claim 1, wherein at least one interferon binding protein is PEGylated.

3. The method of claim 1, wherein at least one interferon binding protein is fused with transferrin.

4. The method of claim 1, wherein said one or more interferon binding proteins has a Kd ranging from about $10^{-3}$ to about $10^{-12}$.

5. The method of claim 1, wherein said administration of a therapeutically effective amount of one or more interferon binding proteins results in the diminution of bioavailable interferon in said patient.

6. The method of claim 1, wherein the activity of Type I interferon, Type II interferon, or a combination thereof is inhibited.

7. The method of claim 1, wherein said disease is selected from the group consisting of Alzheimer's, Down Syndrome, infant encephalitis, AIDS, and an autoimmune disease.

8. The method of claim 7, wherein said disease is Down Syndrome.

9. The method of claim 7, wherein said disease is AIDS.

10. The method of claim 9, wherein said AIDS is HIV-associated dementia.

11. The method of claim 9, wherein said AIDS is HIV-encephalitis.

12. The method of claim 9, wherein at least one interferon binding protein is PEGylated.

13. The method of claim 9, wherein at least one interferon binding protein is fused with transferrin.

14. A method of reducing the incidence of pathological effects of transplant rejection or decreasing the pathological effects of transplant rejection, wherein said pathological effects are associated with excessive levels of one or more interferons in a patient receiving said transplant, comprising administering a therapeutically effective amount of one or more interferon binding proteins to said patient, wherein the one or more interferon binding proteins is selected from the group consisting of B18R, B8R, and a combination thereof.

15. The method of claim 14, wherein at least one interferon binding protein or fragment thereof inhibits the activity of IFN-α, IFN-γ, or both.

16. The method of claim 14, wherein at least one interferon binding protein is PEGylated.

17. The method of claim 14, wherein at least one interferon binding protein is fused with transferrin.

* * * * *